United States Patent
Abraham et al.

(10) Patent No.: US 8,664,352 B2
(45) Date of Patent: Mar. 4, 2014

(54) NATURAL OIL-DERIVED POLYESTER POLYOLS AND POLYURETHANES MADE THEREFROM

(75) Inventors: Timothy Walter Abraham, Minnetonka, MN (US); Jeff J. Malsam, Minneapolis, MN (US)

(73) Assignee: Cargill, Incorporated, Wayzata, MN (US)

( * ) Notice: Subject to any disclaimer, the term of this patent is extended or adjusted under 35 U.S.C. 154(b) by 99 days.

(21) Appl. No.: 12/740,944

(22) PCT Filed: Oct. 31, 2008

(86) PCT No.: PCT/US2008/012379
§ 371 (c)(1),
(2), (4) Date: Apr. 30, 2010

(87) PCT Pub. No.: WO2009/058368
PCT Pub. Date: May 7, 2009

(65) Prior Publication Data
US 2010/0267925 A1    Oct. 21, 2010

Related U.S. Application Data

(60) Provisional application No. 61/001,490, filed on Nov. 1, 2007.

(51) Int. Cl.
*C08G 63/02* (2006.01)
(52) U.S. Cl.
USPC ........................................................ 528/361

(58) Field of Classification Search
None
See application file for complete search history.

(56) References Cited

U.S. PATENT DOCUMENTS

| | | | |
|---|---|---|---|
| 5,512,655 A | 4/1996 | Klauck et al. | |
| 7,833,294 B2 * | 11/2010 | Murphy et al. | 44/275 |
| 2006/0194974 A1 * | 8/2006 | Narayan et al. | 554/133 |
| 2006/0264524 A1 * | 11/2006 | Abraham et al. | 521/172 |
| 2006/0272200 A1 | 12/2006 | Murphy et al. | |
| 2006/0276609 A1 * | 12/2006 | Lysenko et al. | 528/44 |
| 2006/0293400 A1 * | 12/2006 | Wiltz, Jr. et al. | 521/172 |
| 2010/0240860 A1 * | 9/2010 | Abraham et al. | 528/361 |

FOREIGN PATENT DOCUMENTS

WO    WO 2006/118995 A1 *  9/2006

OTHER PUBLICATIONS

U.S. Appl. No. 60/465,685, filed Apr. 25, 2003, Lysenko et al, published in related PCT/US04/12427.*

* cited by examiner

*Primary Examiner* — Randy Gulakowski
*Assistant Examiner* — Jeffrey Washville

(57) ABSTRACT

A polyester polyol made from natural oil feedstocks is disclosed. Methods for making the polyol are also disclosed. The method comprises reacting hydroxylated fatty acid/alkyl esters with a multifunctional ester-reactive initiator compound to form the polyester polyol. In one embodiment, the hydroxylated fatty acid/alkyl esters are made by hydroxylating fatty acid/alkyl esters having up to ninety-five percent by weight monounsaturation.

25 Claims, 4 Drawing Sheets

NATURAL OIL-DERIVED POLYESTER POLYOLS AND POLYURETHANES MADE THEREFROM

CROSS REFERENCE TO RELATED APPLICATION

This application claims the benefit of PCT Patent Application, Serial No. PCT/US2008/012379, filed 31 Oct. 2008, entitled NATURAL OIL-DERIVED POLYESTER POLYOLS AND POLYURETHANES MADE THEREFROM, which claims the benefit of U.S. provisional application Ser. No. 61/001,490 entitled NATURAL OIL-DERIVED POLYESTER POLYOLS AND POLYURETHANES MADE THEREFROM, filed Nov. 1, 2007, which are hereby incorporated by reference in their entirety.

FIELD

This invention relates to polyester polyols that are derived from natural sources such as vegetable oils.

BACKGROUND

Polyols are generally produced from petroleum. Polyols are useful in a variety of applications, as polyols may be used in coatings, adhesives, sealants, elastomers, resins and foams. Polyols may be used in a wide variety of fields including the textile, plastic, medical, chemical, manufacturing, and cosmetic industries.

Research in recent years has focused on alternative, non-petroleum based sources of polyols. One area of focus has been the production of polyols from natural oils, with vegetable oils being of particular focus.

Some examples of non-petroleum based polyols include those described by Petrovic et al. in U.S. Pat. Nos. 6,107,433, 6,433,121, 6,573,354, and 6,686,435. Other examples include those described by Kurth, U.S. Pat. No. 6,180,686.

Although the aforementioned polyols are useful in the production of polymers such as polyurethanes, improved non-petroleum based polyols are also desired. In particular, the ability to control the molecular weight and the functionality of the non-petroleum based polyol is desirable.

SUMMARY

The invention relates to polyester polyols that are derived from natural oils and to polymers (e.g., polyurethane foams) that are made therefrom.

In one aspect, the invention provides polyester polyols having the structure below.

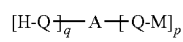

where: A is residue of a multifunctional ester-reactive initiator compound;

p is ≥1;
q is ≥0;
(p+q) is 2 or greater;
-Q- is independently —O— or

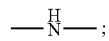

M is selected from:

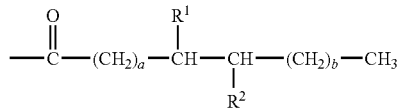

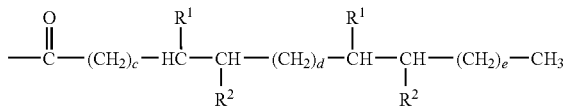

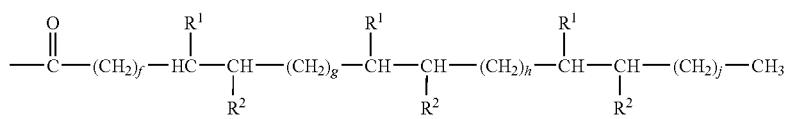

where $-R^1$ and $-R^2$ are independently selected from $-OX$, $-OR$, and $-H$, with the proviso that on vicinal carbon atoms:
one of $-R^1$ or $-R^2$ is $-OX$, and
one of $-R^1$ or $-R^2$ is $-H$;
or
one of $-R^1$ or $-R^2$ is $-OX$, and
one of $-R^1$ or $-R^2$ is $-OR$;

a, b, c, d, e, f, g, h, an j are independently selected integers;
X is H or M; and
R is a straight or branched chain alkyl group, for example, methyl, ethyl, propyl, butyl, and the like.

In exemplary embodiments of the invention, (a+b)=24; (c+d+e)=22; and (f+g+h+j)=20. In one preferred embodiment, (a+b)=14; (c+d+e)=12; and (f+g+h+j)=10.

In another aspect, the invention provides processes for making the polyester polyols from a natural oil-based starting composition. In some embodiments, the polyester polyols are prepared by a process that comprises the steps of:

(a) providing a starting composition comprising up to about 95% weight monounsaturated fatty acid/alkyl esters;
(b) epoxidizing at least a portion of carbon-carbon double bonds in the starting composition to form an epoxidized fatty acid/alkyl ester composition;
(c) reacting the epoxidized fatty acid/alkyl ester composition with an alcohol or hydrogen to ring-open at least a portion of the epoxide groups to form a composition comprising hydroxylated fatty acid/alkyl esters; and
(d) reacting the hydroxylated fatty acid/alkyl ester composition with a multifunctional ester-reactive initiator compound according to the formula $$A\text{-}[Q\text{-}H]_{p+q}$$

where: A is an organic group; with the proviso that A does not contain an ester of a monofunctional alcohol;
(p+q) is an integer greater than or equal to 2; and
-Q-H are independently ester-reactive functional groups, such as alcohols (i.e., -Q- is $-O-$) and amines (i.e., -Q- is $$-\underset{\text{H}}{\text{N}}-);$$

to form the polyester polyol of the invention.

In some embodiments, the polyester polyols are prepared by a process that comprises the steps of:

(a) providing a starting composition comprising monounsaturated fatty acid/alkyl esters; and polyunsaturated fatty acid/alkyl esters;
(b) partially hydrogenating the starting composition to convert at least a portion of the polyunsaturated fatty acid/alkyl esters to monounsaturated fatty acid/alkyl esters; wherein after partial hydrogenation the starting composition comprises up to about 95% weight monounsaturated fatty acid/alkyl ester;
(c) epoxidizing at least a portion of carbon-carbon double bonds in the starting composition to form an epoxidized fatty acid/alkyl ester composition;
(d) reacting the epoxidized fatty acid/alkyl ester composition with an alcohol or hydrogen to ring-open at least a portion of the epoxide groups to form a composition comprising hydroxylated fatty acid/alkyl esters; and
(e) reacting the hydroxylated fatty acid/alkyl ester composition with a multifunctional ester-reactive initiator compound according to the formula $$A\text{-}[Q\text{-}H]_{p+q}$$

where: A is an organic group; with the proviso that A does not contain an ester of a monofunctional alcohol;
(p+q) is an integer greater than or equal to 2; and
-Q-H are independently ester-reactive functional groups, such as alcohols (i.e., -Q- is $-O-$) and amines (i.e., -Q- is $$-\underset{\text{H}}{\text{N}}-);$$

to form the polyester polyol of the invention.

In some embodiments, step (a) comprises the steps of: (a1) providing a natural oil; and (a2) transesterifying or hydrolyzing the natural oil to yield a composition comprising monounsaturated and polyunsaturated fatty acid/alkyl esters.

In yet other embodiments, the polyester polyols are prepared by a process that comprises the steps of:

(a) providing a natural oil;
(b) epoxidizing at least a portion of carbon-carbon double bonds in the natural oil to form an epoxidized natural oil;
(c) reacting the epoxidized natural oil with an alcohol or hydrogen to ring-open at least a portion of the epoxide groups to form a composition comprising a hydroxylated natural oil;
(d) transesterifying or hydrolyzing the hydroxylated natural oil to faun a hydroxylated composition comprising: (i) up to about 95% weight monohydroxylated fatty acid/alkyl esters; and (ii) at least one of saturated fatty acid/alkyl esters or polyhydroxylated fatty acid/alkyl esters; and
(e) reacting the hydroxylated composition with a multifunctional ester-reactive initiator compound according to the formula $$A\text{-}[Q\text{-}H]_{p+q}$$

where: A is an organic group; with the proviso that A does not contain an ester of a monofunctional alcohol;
(p+q) is an integer greater than or equal to 2; and
-Q-H are independently ester-reactive functional groups, such as alcohols (i.e., -Q- is $-O-$) and amines (i.e., -Q- is $$-\underset{\text{H}}{\text{N}}-);$$

to form the polyester polyol of the invention.

In yet another aspect the invention provides polymers (e.g., polyesters, polyurethanes, and polycarbonates) that are prepared from the polyester polyols of the invention. In an exemplary embodiment, the polymers are polyurethanes that comprise the reaction product of (a) a polyisocyanate; and (b) a polyester polyol of the invention. The polyurethanes may be polyurethane foams such as flexible slabstock foams or molded foams.

DETAILED DESCRIPTION

The invention relates to polyester polyols that are derived from natural oil starting materials and to polymers (e.g., polyurethane foams) that are made using the polyester polyols.

Exemplary methods of making the polyester polyols of the invention will now be described with reference to FIGS. 1-4.

Figure 1:
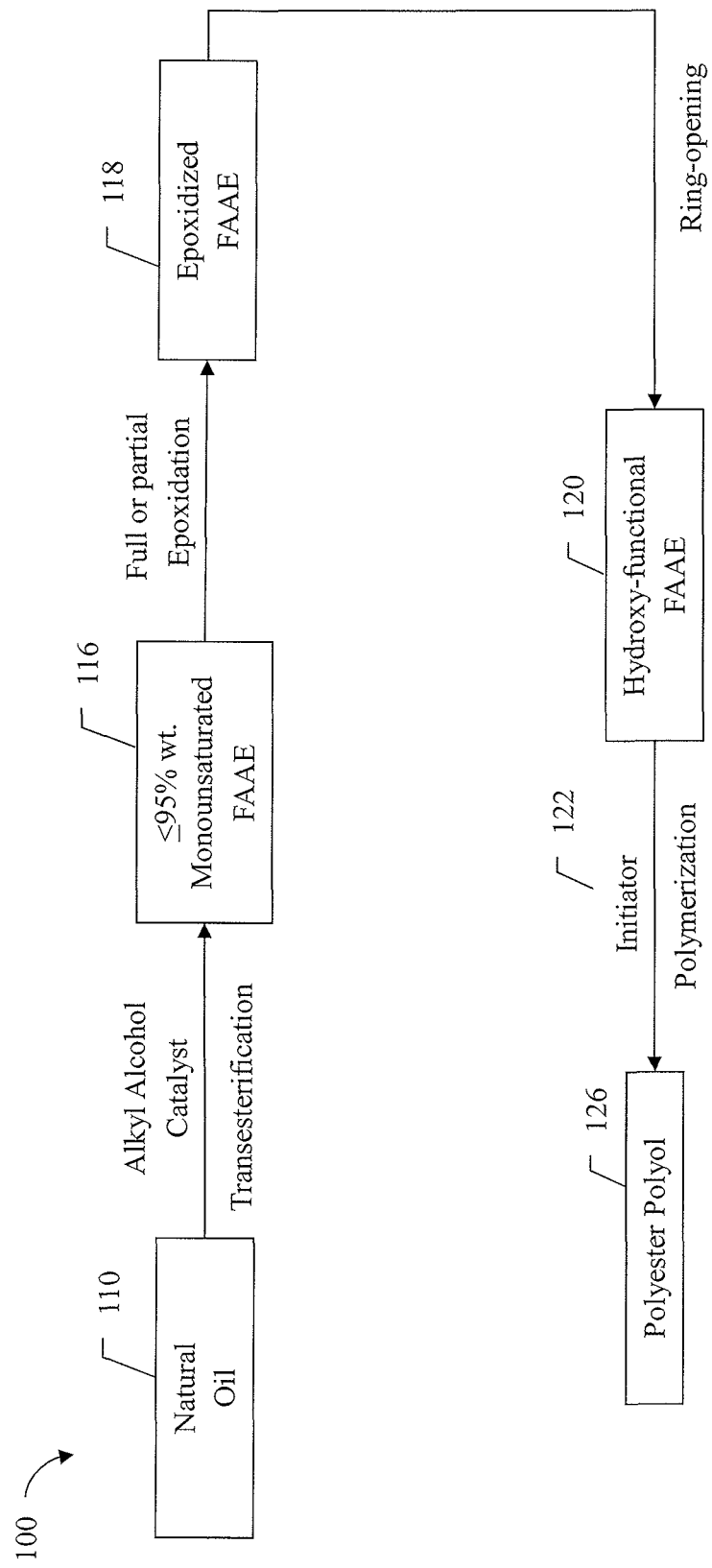
FIG. 1 is an exemplary reaction scheme to produce a polyester polyol of the invention.

Referring now to FIG. 1, an exemplary reaction scheme 100 for preparing polyester polyols of the invention is provided. In process 100 a natural oil 110 is first transesterified with an alkyl alcohol in the presence of a transesterification catalyst to produce a composition comprising up to about 95% weight monounsaturated fatty acid alkyl esters (FAAE) 116. The fatty acid alkyl ester composition 116 is then fully or partially epoxidized to form an epoxidized fatty acid alkyl ester composition 118. The epoxidized fatty acid alkyl ester composition 118 is then ring-opened (e.g., by reaction with an alcohol or hydrogenation) to form a composition comprising hydroxy-functional fatty acid alkyl esters 120. The hydroxy-functional fatty acid alkyl ester composition 120 is then polymerized with an ester-reactive initiator 122 in order to form polyester polyol 126.

Figure 2:
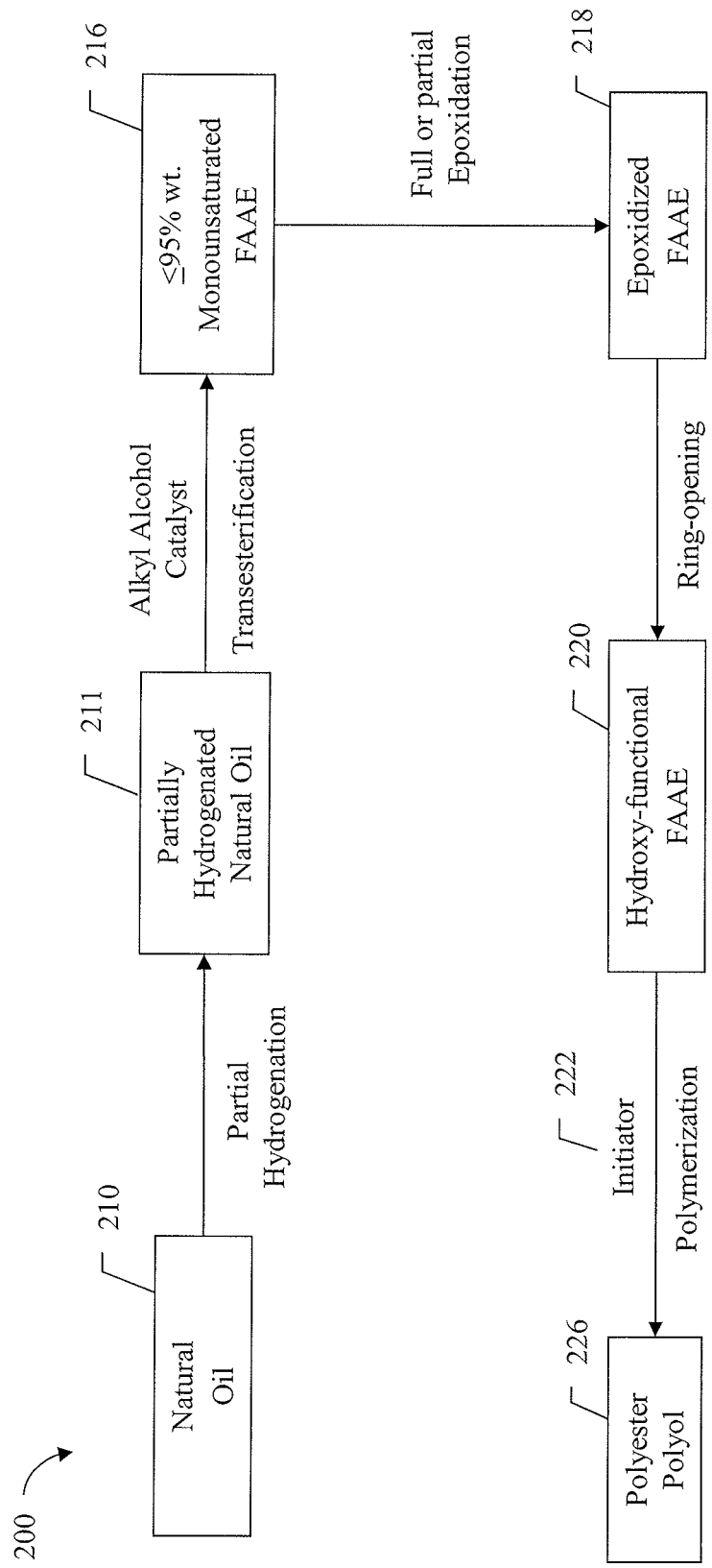
FIG. 2 is an exemplary reaction scheme to produce a polyester polyol of the invention.

Referring now to FIG. 2, another exemplary reaction scheme 200 for preparing polyester polyols of the invention is shown. In process 200 a natural oil 210 is first partially hydrogenated in order to produce partially hydrogenated natural oil 211. Partially hydrogenated natural oil 211 is then transesterified with an alkyl alcohol in the presence of a transesterification catalyst to produce a composition comprising up to about 95% weight monounsaturated fatty acid alkyl esters 216. The fatty acid alkyl ester composition 216 is then fully or partially epoxidized to form an epoxidized fatty acid alkyl ester composition 218. The epoxidized fatty acid alkyl ester composition 218 is then ring-opened (e.g., by reaction with an alcohol or hydrogenation) to form a composition comprising hydroxy-functional fatty acid alkyl esters 220. The hydroxy-functional fatty acid alkyl ester composition 220 is then reacted with an ester-reactive initiator 222 in order to form polyester polyol 226.

Figure 3:
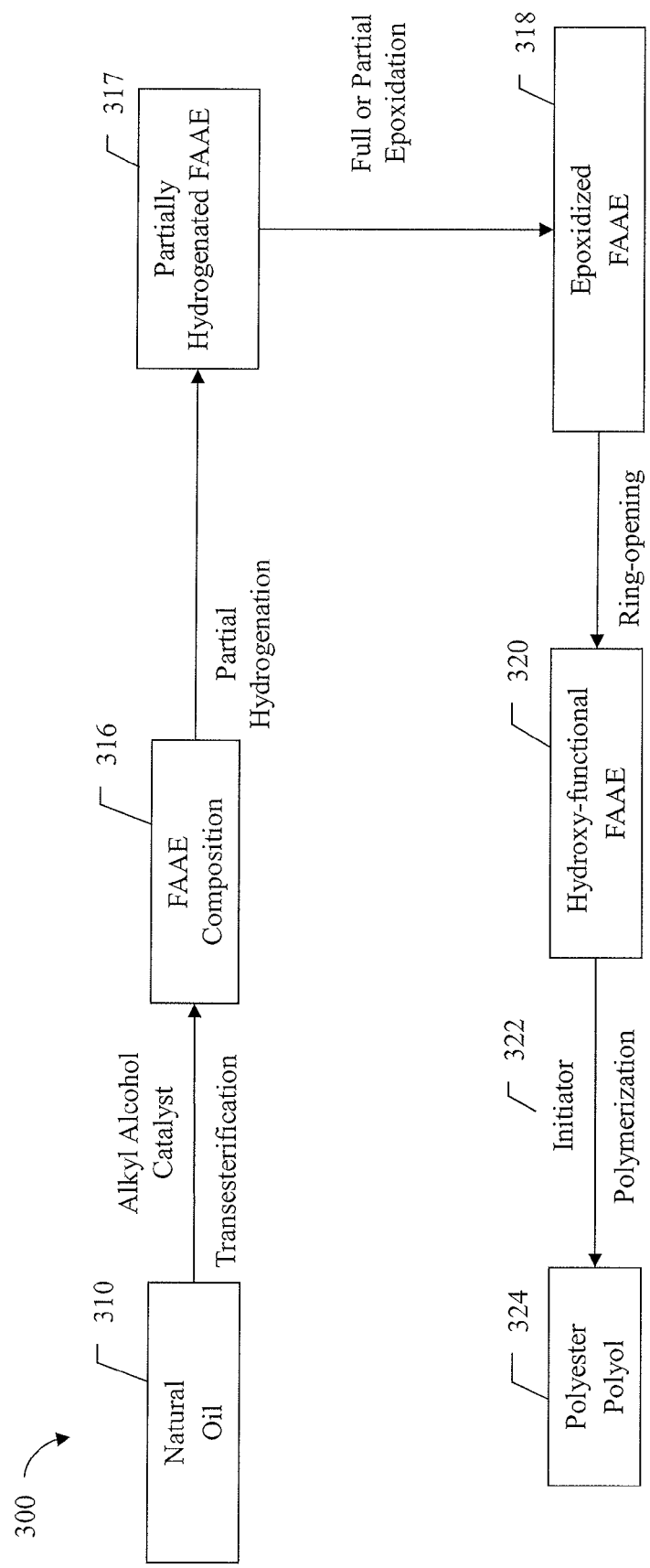
FIG. 3 is an exemplary reaction scheme to produce a polyester polyol of the invention.

Referring now to FIG. 3, another exemplary reaction scheme 300 for preparing polyester polyols of the invention is shown. In this variation, a natural oil 310 is first transesterified with an alkyl alcohol in the presence of a transesterification catalyst to produce a fatty acid ester composition 316. The fatty acid ester composition 316 is then partially hydrogenated to increase the monounsaturated fatty acid ester content resulting in partially hydrogenated fatty acid ester composition 317. Typically, composition 317 comprises up to about 95% weight monounsaturated fatty acid alkyl esters. The partially hydrogenated fatty acid alkyl ester composition 317 is then fully or partially epoxidized to form an epoxidized fatty acid alkyl ester composition 318. The epoxidized fatty acid alkyl ester composition 318 is then ring-opened (e.g., by reaction with an alcohol or hydrogenation) to form a composition comprising hydroxy-functional fatty acid alkyl esters 320. The hydroxy-functional fatty acid alkyl ester composition 320 is then reacted with an ester-reactive initiator 322 in order to form polyester polyol 324.

Figure 4:
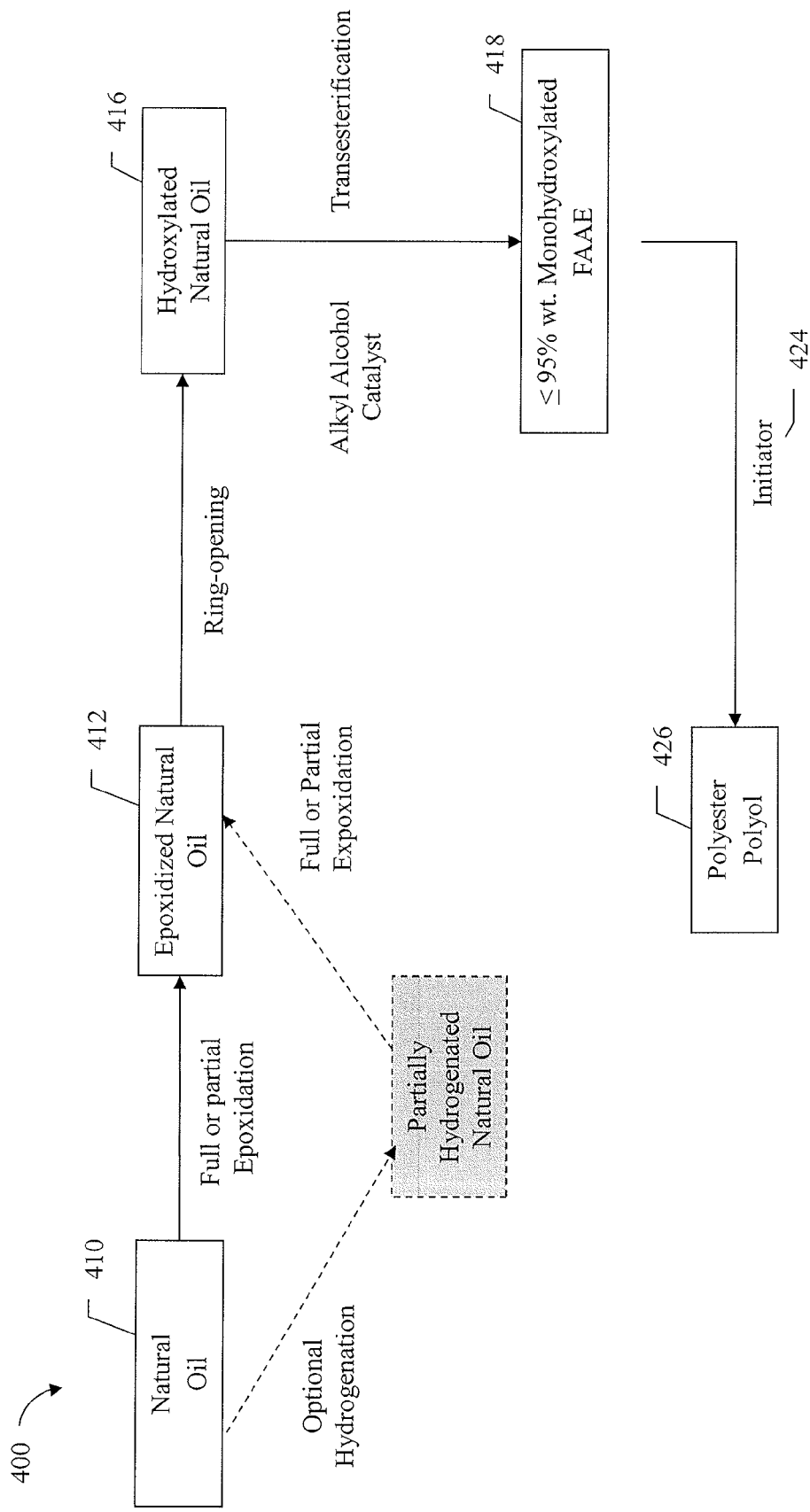
FIG. 4 is an exemplary reaction scheme to produce a polyester polyol of the invention.

Referring now to FIG. 4, another exemplary reaction scheme 400 is shown. In process 400, the natural oil 410 is first epoxidized to form an epoxidized natural oil 412. Optionally, prior to epoxidation, the natural oil may be partially hydrogenated in order to increase the content of monounsaturated fatty ester in the partially hydrogenated natural oil 411. Next, the epoxidized natural oil 412 is reacted with alcohol or hydrogen to ring-open at least a portion of the epoxide groups thereby forming a composition 416 comprising a hydroxylated natural oil. Following this, the hydroxylated natural oil 416 is transesterified or hydrolyzed to form a composition 418 comprising up to about 95% weight monohydroxylated fatty acid/alkyl esters. The hydroxylated fatty acid/alkyl ester 418 is then reacted with an ester-reactive initiator 424 in order to form polyester polyol 426.

Starting Composition:

Starting materials that are useful for preparing the polyester polyols of the invention comprise a monounsaturated fatty acid/alkyl ester composition. In some embodiments, the starting materials comprise a high content of monounsaturated fatty acids/alkyl esters. Preferably, the fatty acid/alkyl esters are alkyl esters of fatty acids (hereinafter referred to as "fatty acid alkyl esters"). The fatty acid alkyl esters are preferred due to their ability to be readily polymerized compared to their fatty acid analogs. By "monounsaturated fatty acid/alkyl ester composition" it is meant that the composition comprises monounsaturated fatty acids, monounsaturated fatty acid alkyl esters, or mixtures thereof. By the term "monounsaturated" it is meant that a fatty acid or fatty acid alkyl ester has one carbon-carbon double bond that is located in the main chain of the fatty acid or fatty ester. The starting composition also may include saturated fatty acid/alkyl esters. By the to term "saturated" it is meant that the fatty acid/alkyl ester has a saturated main chain that includes only carbon-carbon single bonds connecting the carbon atoms. The starting composition also typically includes polyunsaturated fatty acid/alkyl esters. By the term "polyunsaturated" it is meant that the fatty acid/alkyl ester has a main chain that includes two or more carbon-carbon double bonds.

In many embodiments, the starting material is derived from a natural oil, such as a vegetable oil or animal fat. In some embodiments the natural oil is transesterified with a monofunctional alcohol or is hydrolyzed in order to yield alkyl esters or acids of the various fatty acids that are present in the natural oil. Natural oils that may be used to prepare the starting compositions typically comprise monounsaturated fatty acids and polyunsaturated fatty acids that are esterified to glycerol to form glycerides, typically triglycerides. The fatty acids typically contain chain lengths that have from about 12 to about 24 carbon atoms. Common saturated fatty acids that are present in the natural oils include lauric acid (dodecanoic acid), myristic acid (tetradecanoic acid), palmitic acid (hexadecanoic acid), stearic acid (octadecanoic acid), arachidic acid (eicosanoic acid), and lignoceric acid (tetracosanoic acid). Common monounsaturated fatty acids include palmitoleic acid (a C16 unsaturated acid) and oleic acid (a C18 unsaturated acid). Common polyunsaturated fatty acids include linoleic acid (a C18 di-unsaturated acid), linolenic acid (a C18 tri-unsaturated acid), and arachidonic acid (a C20 tetra-unsaturated acid).

Examples of natural oils include plant-based oils (e.g., vegetable oils) and animal fats. Useful natural oil sources include canola oil, tall oil, soybean oil, safflower oil, linseed oil, corn oil, sunflower oil, olive oil, canola oil, sesame oil, cottonseed oil, palm-based oils, rapeseed oil, tung oil, peanut oil, jatropha oil, and combinations thereof. Animal fats may also be used, for example, fish oil, lard, and tallow. The plant-based oils may be natural or genetically modified vegetable oils, for example, high oleic safflower oil, high oleic soybean oil, high oleic canola oil, high oleic peanut oil, high oleic sunflower oil, and high erucic rapeseed oil (crambe oil). Also included are microbial oils, such as algal oil, including those that are genetically modified to increase yields and/or to obtain selective fatty acid distributions.

In many embodiments, the staring composition comprises a relatively high amount of monounsaturated fatty acid/ester relative to the amount of saturated fatty acid/ester and polyunsaturated fatty acid/ester. The high amount of monounsaturated fatty acid/ester may be present in the natural oil itself or it may be obtained by chemical modification of the natural oil such as partial hydrogenation.

In some embodiments, the starting composition comprises up to about 95% weight monounsaturated fatty acids/alkyl esters. In other embodiments, the starting composition comprises from about 20% weight to about 95% weight monounsaturated fatty acids/alkyl esters. Preferably, the composition comprises from 65-94 wt % monounsaturated fatty acids/alkyl esters, more preferably, from 70-90 wt %, and furthermore preferably from 80-85 wt % monounsaturated fatty acids/alkyl esters.

In some embodiments of the invention, the starting material is a natural oil (or is derived from a natural oil) that is high in monounsaturated fatty acid/alkyl ester, examples include canola oil, high oleic sunflower oil, and tall oil.

In some embodiments, the starting material is partially hydrogenated in order to increase the relative amount of monounsaturated fatty acids/alkyl esters that are present relative to polyunsaturated fatty acids/alkyl esters. In this way, natural oils that are lower in monounsaturated fatty acids (e.g., soybean oil) may be used in the present invention. Methods for hydrogenation of natural oils are well known in the art and include, for example, contact with hydrogen gas in the presence of a nickel catalyst. During hydrogenation, polyunsaturated fatty acid/alkyl ester species in the starting composition are converted to monounsaturated fatty acids/alkyl esters and some saturated fatty acids/alkyl esters. Preferably, the hydrogenation increases the amount of monounsaturated fatty acids/alkyl esters relative to polyunsaturated fatty acids/alkyl esters, while not substantially increasing the saturated fatty acid/alkyl ester content. For example, in some embodiments, the monounsaturated fatty acids/alkyl esters are increased to a level of about 70% weight or greater, and the polyunsaturated fatty acids/alkyl esters are reduced to about 10% weight or less. In some embodiments, after hydrogenation the saturated fatty acids/alkyl esters are present in an amount of about 20% weight or less. For example, for soybean oil partial hydrogenation typically increases the amount of saturated fatty acids from about 15% weight to about 20% weight or greater.

Representative examples of monounsaturated fatty acids/alkyl esters include C5-C6, C6-C7, C9-C10, and C11-C12 monounsaturated fatty acids/alkyl esters. As used herein the term "C9-C10 monounsaturated" refers to a fatty acid/alkyl ester having one carbon-carbon double bond located between the $9^{th}$ and $10^{th}$ carbon atoms (i.e., between C9 and C10) in the alkene chain of the monounsaturated fatty acid/alkyl ester. In determining this position, the alkene chain is numbered beginning with the carbon atom in the carbonyl group of the monounsaturated fatty acid/alkyl ester. In many embodiments, a C9-C10 monounsaturated fatty acid/alkyl ester may be represented by the following structure:

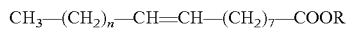

$$CH_3-(CH_2)_n-CH=CH-(CH_2)_7-COOR$$

where n is ≥0, more typically ranging from 1 to 13; and
R is hydrogen (fatty acid) or a straight or branched chain alkyl group, more typically a methyl, ethyl, propyl, butyl, and the like.

As used herein the term "C5-C6 monounsaturated" refers to a monounsaturated fatty acid/alkyl ester that has one carbon-carbon double bond located between the $5^{th}$ and $6^{th}$ carbon atoms (i.e., between C5 and C6) in the alkene chain of the monounsaturated fatty acid/alkyl ester. A C5-C6 monounsaturated fatty acid/alkyl ester may be represented by the following structure:

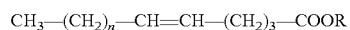

$$CH_3-(CH_2)_n-CH=CH-(CH_2)_3-COOR$$

where n is ≥0, more typically ranging from 1 to 17; and
R is hydrogen or a straight or branched chain alkyl group, more typically a methyl, ethyl, propyl, butyl, and the like.

Useful natural oil sources for C5-C6 monounsaturated fatty acid/alkyl ester includes meadowfoam oil which contains a twenty carbon C5-C6 monounsaturated fatty acid in glyceride form.

As used herein the term "C6-C7 monounsaturated" refers to a FAAE having one carbon-carbon double bond located between the $6^{th}$ and $7^{th}$ carbon atoms (i.e., between C6 and C7) in the alkene chain of the monounsaturated fatty acid alkyl ester. A C6-C7 monounsaturated fatty acid alkyl ester may be represented by the following structure:

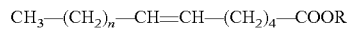

$$CH_3-(CH_2)_n-CH=CH-(CH_2)_4-COOR$$

where n is ≥0, more typically ranging from 2 to 16; and
R is a straight or branched chain alkyl group, more typically a methyl, ethyl, propyl, butyl, and the like.

Useful natural oil sources for C6-C7 monounsaturated fatty acids include coriander oil which contains an 18 carbon unsaturated fatty acid (C18:1; Δ6) in glyceride form.

As used herein the term "C11-C12 monounsaturated" refers to a fatty acid/alkyl ester having one carbon-carbon double bond located between the $11^{th}$ and $12^{th}$ carbon atoms (i.e., between C11 and C12) in the alkene chain of the monounsaturated fatty acid/alkyl ester. A C11-C12 monounsaturated fatty acid/alkyl ester may be represented by the following structure:

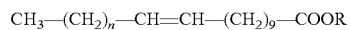

$$CH_3-(CH_2)_n-CH=CH-(CH_2)_9-COOR$$

where n is ≥0, more typically ranging from 1 to 11; and
R is hydrogen or a straight or branched chain alkyl group, more typically a methyl, ethyl, propyl, butyl, and the like.

Useful natural oil sources for C11-C12 monounsaturated fatty acids include camelina oil which contains gondoic acid (C20:1 Δ11) at approximately 15% of the fatty acid composition.

As used herein the term "C13-C14 monounsaturated" refers to a fatty acid/alkyl ester having one carbon-carbon double bond located between the $13^{th}$ and $14^{th}$ carbon atoms (i.e., between C13 and C14) in the alkene chain of the monounsaturated fatty acid/alkyl ester. A C13-C14 monounsaturated fatty acid/alkyl ester may be represented by the following structure:

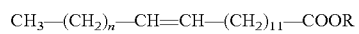

$$CH_3-(CH_2)_n-CH=CH-(CH_2)_{11}-COOR$$

where n is ≥0, more typically ranging from 1 to 9; and
R is hydrogen or a straight or branched chain alkyl group, more typically a methyl, ethyl, propyl, butyl, and the like.

Useful natural oil sources for C13-C14 monounsaturated fatty acids include crambe oil, fish oil, and high erucic acid rapeseed oil, which are high in erucic acid in glyceride form.

In some embodiments, the starting material comprises a natural oil that contains epoxidized fatty acids. Examples of such epoxidized fatty acids include vernolic acid, alchornoic acid, and coronaric acid.

Epoxidation:

In some embodiments of the invention, the starting composition is epoxidized and ring-opened in order to convert at least a portion of the double bonds that are present in the fatty acids/alkyl esters into hydroxyl groups. More specifically, the introduction of hydroxyl functionality is accomplished by first epoxidizing at least a portion of the carbon-carbon double bonds in the fatty acids/alkyl esters followed by ring-opening of the epoxide groups to form hydroxyl groups.

Epoxidation is typically accomplished by reacting the fatty acid/alkyl ester composition with a peroxyacid under conditions that convert at least a portion of or all of the carbon-carbon double bonds to epoxide groups. Examples of peroxyacids include peroxyformic acid, peroxyacetic acid, trifluoroperoxyacetic acid, benzyloxyperoxyformic acid, 3,5-dinitroperoxybenzoic acid, m-chloroperoxybenzoic acid, and combinations thereof. In some embodiments, peroxyformic acid or peroxyacetic acid are used. The peroxyacids may be added directly to the reaction mixture, or they may be formed in-situ by reacting a hydroperoxide with a corresponding acid such as formic acid, benzoic acid, fatty acids (e.g., oleic acid), or acetic acid. Examples of hydroperoxides that may be used include hydrogen peroxide, tert-butylhydroperoxide, triphenylsilylhydroperooxide, cumylhydroperoxide, and combinations thereof. In an exemplary embodiment, hydrogen peroxide is used.

Typically, for in-situ peroxyacid formation, the amount of acid used to form the peroxyacid ranges from about 0.25 to about 1.0 moles of acid per mole of double bonds in the fatty acid/ alkyl ester composition, more typically ranging from about 0.45 to about 0.55 moles of acid per mole of double bonds in the fatty acid/alkyl ester composition. Typically, the amount of hydrogen peroxide used to form the peroxy acid is about 0.5 to about 1.5 moles of hydrogen peroxide per mole of double bonds in the fatty acid/alkyl ester composition, more typically about 0.8 to about 1.2 moles of hydrogen peroxide per mole of double bonds in the fatty acid/alkyl ester composition.

Typically, an additional acid component is also present in the reaction mixture. Examples of such additional acids include sulfuric acid, toluenesulfonic acid, trifluoroacetic acid, fluoroboric acid, Lewis acids, acidic clays, or acidic ion exchange resins.

Optionally, a solvent may be added to the reaction. Useful solvents include chemically inert solvents, for example, aprotic solvents. These solvents do not include a nucleophile and are non-reactive with acids. Hydrophobic solvents, such as aromatic and aliphatic hydrocarbons, are particularly desirable. Representative examples of suitable solvents include benzene, toluene, xylene, hexane, isohexane, pentane, heptane, and chlorinated solvents (e.g., carbon tetrachloride). In an exemplary embodiment, toluene is used as the solvent. Solvents may be used to reduce the speed of reaction or to reduce the number of side reactions. In general, a solvent also acts as a viscosity reducer for the resulting composition.

Subsequent to the epoxidation reaction, the reaction product may be neutralized. A neutralizing agent may be added to neutralize any remaining acidic components in the reaction product. Suitable neutralizing agents include weak bases, metal bicarbonates, or ion-exchange resins. Examples of neutralizing agents that may be used include ammonia, calcium carbonate, sodium bicarbonate, magnesium carbonate, amines, and ion-exchange resin, as well as aqueous solutions of neutralizing agents. Typically, the neutralizing agent will be an anionic ion-exchange resin. One example of a suitable weakly-basic ion-exchange resin is sold under the trade designation "LEWATIT MP-64" (from Bayer). If a solid neutralizing agent (e.g., ion-exchange resin) is used, the solid neutralizing agent may be removed from the epoxidized vegetable oil by filtration. Alternatively, the reaction mixture may be neutralized by passing the mixture through a neutralization bed containing a resin or other materials. Alternatively, the reaction product may be repeatedly washed to separate and remove the acidic components from the product. In addition, one or more of the processes may be combined in neutralizing the reaction product. For example, the product could be washed, neutralized with a resin material, and then filtered.

Subsequent to the epoxidation reaction, excess solvents may be removed from the reaction product. The excess solvents include products given off by the reaction, or those added to the reaction. The excess solvents may be removed by separation, vacuum, or other method. Preferably, the excess solvent removal will be accomplished by exposure to vacuum.

Ring-Opening of Epoxides

After epoxidation, the epoxide groups are ring-opened in order to convert at least a portion of the epoxide groups to hydroxyl groups. In this way, the epoxidized fatty acids/alkyl esters are converted into a hydroxyl-functional fatty acids/alkyl esters. In some embodiments, the ring-opening is accomplished by reacting the epoxidized fatty acid/alkyl ester composition with a ring-opening nucleophile in the presence of a ring-opening acid catalyst. In other embodiments, the ring-opening is accomplished by hydrogenating the epoxide groups to produce a hydroxyl group.

Various ring-openers may be used, such as alcohols. In many embodiments the ring-opener is a monohydric alcohol. Examples include methanol, ethanol, propanol (including n-propanol and isopropanol), and butanol (including n-butanol and isobutanol), and monoalkyl ethers of ethylene glycol (e.g., methyl cellosolve, butyl cellosolve, and the like). In exemplary embodiments, the ring-opener is methanol.

The ring-opening reaction is typically conducted with an excess of ring-opener to avoid the formation of polyether oligomers. For example, in some embodiments, about 3 moles or greater of ring-opener is used per mole of epoxide. In other embodiments, about 5 moles or greater of ring-opener is used per mole of epoxide. In yet other embodiments, about 10 moles or greater of ring-opener is used per mole of epoxide.

The ring-opening reaction may be monitored using known techniques, for example, hydroxyl number titration (ASTM E1899-02), EOC titration (AOCS Cd9-57 method) or monitoring the heat removed from the exothermic reaction. As used herein "epoxy oxygen content" or "EOC" refers to the weight of epoxide oxygen in a molecule expressed as a percentage.

Upon completion of the ring-opening reaction, any unreacted ring-opener (e.g., methanol) may be removed, for example, by vacuum distillation. Unreacted methanol is not desirable in the polyester polyol because it is a monofunctional species that will end-cap the polyisocyanate.

Representative examples of ring-opening acid catalysts include Lewis or Brönsted acids. Examples of Brönsted acids include hydrofluoroboric acid ($HBF_4$), triflic acid, sulfuric acid, hydrochloric acid, phosphoric acid, phosphorous acid, hypophosphorous acid, boronic acids, sulfonic acids (e.g., para-toluene sulfonic acid, methanesulfonic acid, and trifluoromethane sulfonic acid), and carboxylic acids (e.g., formic acid and acetic acid). Examples of Lewis acids include aluminum halides (for example, aluminum trichloride) phosphorous halides (for example, phosphorus trichloride) and boron halides (e.g., boron trifluoride). Ion exchange resins in the protic form may also be used. In an exemplary embodiment, the ring-opening catalyst is hydrofluoroboric acid (HBF$_4$). The ring-opening catalyst is typically present in an amount ranging from about 0.01% weight to about 0.3% weight, more typically ranging from about 0.05% weight to about 0.15% weight based upon the total weight of the reaction mixture.

Ring-opening may also be accomplished by hydrogenating the epoxide groups to produce hydroxyl groups. Hydrogenation of epoxidized fatty acid esters is described, for example, in U.S. Pat. No. 3,778,465 (Barnstorf).

Polymerization

After synthesis of the hydroxyl-functional fatty acids/alkyl esters, the hydroxyl-functional fatty acids/alkyl esters are reacted with an initiator molecule (i.e., a multifunctional ester-reactive compound) to form the polyester polyol of the invention. The initiator molecule is a multifunctional ester-reactive compound having two or more reactive groups that are capable of reacting with ester groups that are present on the hydroxyl-functional fatty acids/alkyl esters. In many embodiments, the initiator compound has the structure:

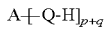

where: A is an organic group; with the proviso that A does not contain an ester of a monofunctional alcohol;
(p+q) is an integer greater than or equal to 2; and
-Q-H are independently ester-reactive functional groups, such as alcohols (i.e., -Q- is —O—) and amines (i.e., -Q- is

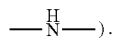

).

Examples of initiators include polyols, polyamines, and aminoalcohols.

Exemplary polyol initiators include neopentylglycol; 1,2-propylene glycol; 1,3-propanediol, trimethylolpropane; pentaerythritol; sorbitol; sucrose; glycerol; alkanediols such as 1,6-hexanediol; 2,5-hexanediol; 1,4-butanediol; 1,4-cyclohexane diol; ethylene glycol; diethylene glycol; triethylene glycol; tetraethylene glycols, and other polyetheyleneglycols, 9(1)-hydroxymethyloctadecanol, 1,4-bishydroxymethylcyclohexane, Dimerol alcohol (36 carbon diol available from Henkel Corporation); bisphenol A, hydrogenated bisphenol; 1,2,6-hexanetriol; ethanolamine; diethanolamine; triethanolamine; any of the aforementioned where at least one of the alcohol or amine groups present therein has been reacted with ethylene oxide, propylene oxide, or butylene oxide and/or mixtures thereof. Also useful as initiators are natural oil based polyols such as those produced by epoxidation and ring-opening of natural oils, for example, vegetable oils. Exemplary natural oil based polyols are described in U.S. Pat. Nos. 6,573,354; 6,107,433; 6,433,121; 6,686,435; and U.S. Patent Publication Nos. 2006/0264524; and 2006/0041157.

In some embodiments, the polyol initiators comprise hydroxylated fatty acids that have been esterified with polyalcohols.

Polymerization of the initiator with the starting composition is typically performed until little or no esters of the starting composition are present in the final product.

The use of multifunctional initiators (as described above) along with the control of the ratio of the initiator to the starting composition allows control of the molecular weight, functionality, and viscosity of the resulting polyol.

Exemplary polyamine initiators include ethylene diamine; neopentyldiamine, 1,6-diaminohexane; bisaminomethyltricyclodecane; bisaminocyclohexane; diethylene triamine; bis-3-aminopropyl methylamine; and triethylene tetramine.

Exemplary aminoalcohols initiators include ethanolamine, diethanolamine, and triethanolamine.

Other useful compounds that may be used as initiators include, for example, polyols, polyamines or aminoalcohols described in U.S. Pat. Nos. 4,216,344; 4,243,818 and 4,348,543 and British Pat. No. 1,043,507.

Preferably, the initiator is selected from the group consisting of neopentylglycol; trimethylolpropane; pentaerythritol; sorbitol; sucrose; glycerol; 1,2-propylene glycol; 1,3-propanediol,1,6-hexanediol; 2,5-hexanediol; 1,6-hexanediol; 1,4-cyclohexane diol; 1,4-butanediol; ethylene glycol; diethylene glycol; triethylene glycol; polyethylene glycol, bis-3-aminopropyl methylamine; ethylene diamine; diethylene triamine; 9(1)-hydroxymethyloctadecanol; 1,4-bishydroxymethylcyclohexane; Dimerol alcohol; hydrogenated bisphenol; 1,2,6-hexanetriol; any of the aforementioned where at least one of the alcohol or amine groups present therein has been reacted with ethylene oxide, propylene oxide or mixture thereof; and combination thereof.

Most preferably the initiator is trimethylolpropane, glycerol, pentaerythritol, sucrose, sorbitol, an ethoxylated glycerol, propoxylated glycerol, ethoxylated pentaerythritol, propoxylated pentaerythritol, or mixtures thereof.

Polyester polyols of the invention may be synthesized according to two general reaction sequences. In a first sequence, the hydroxyl-functional fatty acids/alkyl esters and the initiator are reacted with one another directly. In a second reaction sequence, the hydroxyl-functional fatty acids/alkyl esters are pre-reacted with each other (i.e., the hydroxyl-functional fatty acids/alkyl esters are polymerized), and the resulting polymerized hydroxy-functional fatty acids/alkyl esters is then reacted with the initiator to form the polyester polyol of the invention.

In many embodiments, the polyester polyol of the invention is formed by reacting an initiator with an excess of hydroxyl-functional fatty acids/alkyl esters. The acid/ester groups of the hydroxyl-functional fatty acids/alkyl esters react with the ester-reactive groups of the initiator. This reaction results in the formation of an ester or amide group, which couples the initiator to hydroxyl-functional fatty acids/alkyl esters. The pendant hydroxyl group(s) on the coupled hydroxyl-functional fatty acids/alkyl esters may then react with an ester group on another molecule of hydroxyl-functional fatty acid/alkyl ester thereby resulting in the formation of ester groups that couple the molecules together. Continued polymerization of the hydroxyl-functional fatty acids/alkyl esters results in the formation of polyester segments extending from the initiator molecule. Typically, the polyester segments contain a terminal hydroxyl-functional fatty acid alkyl ester, which provides hydroxyl functionality to the polyester polyol. In some embodiments, the polyester segment may contain a terminal polyhydroxylated fatty acid alkyl ester, or a terminal saturated fatty acid alkyl ester. In the case of a terminal saturated fatty acid alkyl ester, the segment will not contain a hydroxyl group thereby decreasing the functionality and OH number of the polyol. In the case of a terminal polyhydroxylated fatty acid, the segment will contain multiple hydroxyl groups thereby increasing the functionality and OH number of the polyol.

Typically, the hydroxyl-functional fatty acids/alkyl esters and the initiator are heated to a desired reaction temperature, for a desired reaction time. In many embodiments, the reaction is conducted under vacuum and in the presence of a catalyst. Useful catalysts include, for example, tin, titanium, enzyme catalyst (e.g., lipase), carbonate catalyst (e.g., $K_2CO_3$, $NaHCO_3$), alkali metal alkoxides (e.g., NaOMe, KOMe, KO$^t$Bu) or combinations thereof. Acid catalyst may also be used, but may result in competing dehydration reactions.

The reaction temperature that is employed typically ranges from about 140° C. to about 300° C. when using a tin, titanium, or alkali metal-based catalyst. Preferably, the reaction temperature is at least about 150° C., more preferably at least about 180° C., most preferably at least about 190° C. Preferably, the reaction temperature is about 250° C. or less, more preferably at 220° C. or less, and most preferably about 210° C. or less. Enzymes usually require temperatures from room temperature up to about 100° C.

The reaction time typically ranges from about 10 minutes to about 24 hours. Preferably, the reaction time ranges from about 15 minutes, more typically about 30 minutes, more typically about 1 hour to preferably about 12 hours, more typically about 9 hours and most typically about 5 hours.

In many embodiments, the reaction is carried out under a vacuum. Typically, the vacuum is at least about 100 torr, more preferably at least about 50 torr, and most preferably at least about 20 torr.

In a preferred embodiment, the hydroxyl-functional acids alkyl esters are placed in the reactor under vacuum at the reaction temperature for a period of time sufficient to polymerize a substantial amount of the hydroxyl-functional fatty acids/alkyl esters (e.g., at least about 10 percent of the ester groups of the hydroxyl-functional fatty acids alkyl esters have undergone polymerization) and subsequently the initiator is added to form the polyester polyol.

Generally, when a tin catalyst is employed, the amount of catalyst is at least about 100 ppm to at most about 2500 ppm by weight of tin to the total reaction mixture. Preferably, the amount of tin catalyst is at least about 250 ppm, more preferably at least about 500 ppm and most preferably at least about 1000 ppm to preferably at most about 2000 ppm, more preferably at most about 1500 ppm. The tin catalyst may be any suitable tin catalyst such as those known in the art. Exemplary tin catalysts include tin (II) octanoate, tin (II) 2-ethylheptanoate, dibutyl tin (IV) dilaurate, and other tin catalysts which are similarly functionalized. Preferably the tin catalyst is tin (II) octanoate, tin (II) 2-ethylheptanoate, dibutyl tin (IV) dilaurate or combination thereof.

Generally, when a titanium catalyst is employed, the amount of catalyst is at least about 100 ppm to at most about 2500 ppm by weight of titanium to the total reaction mixture. Preferably, the amount of titanium catalyst is at least about 250 ppm, more preferably at least about 500 ppm and most preferably at least about 1000 ppm to preferably at most about 2000 ppm, more preferably at most about 1500 ppm. The titanium catalyst may be any suitable catalyst such as those known in the art. Exemplary titanium catalysts include titanium tetraisopropoxide, titanium tetraisobutoxide, or any appropriately functionalized titanium (IV) alkoxide. Preferably the titanium catalyst is titanium tetraisopropoxide.

The ratio of ester groups in the hydroxyl-functional fatty acids/alkyl esters to ester-reactive groups in the initiator typically ranges from about 1:1 (e.g., if the initiator is 1 mole of trimethylolpropane, the amount of hydroxyl-functional fatty acids/alkyl esters is 3 moles) to about 100:1. In some embodiments, the ratio is about 2:1 or greater, more typically about 5:1 or greater, even more typically about 7:1 or greater, and most typically about 10:1 or greater. In some embodiments, the ratio is about 50:1 or less, more typically about 25:1 or less, and most typically about 20:1 or less.

The molecular weight of the polyester polyol may be controlled, for example, by controlling the molar ratio of the hydroxyl-functional fatty acids/alkyl esters to the initiator. More specifically, as the molar ratio of the hydroxyl-functional fatty acids/alkyl esters to the initiator increases, the molecular weight of the polyester polyol increases (assuming that the reaction is brought to completion). In many embodiments, the molar ratio of the hydroxyl-functional fatty acids/alkyl esters to the initiator ranges from about 1 to about 100, more typically about 3 to about 25.

In many embodiments the polyester polyol of the invention can be represented by the structure shown below.

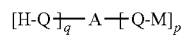

where: A is residue of the initiator;
p is ≥1;
q is ≥0;
(p+q) is 2 or greater;
-Q- is selected from —O— or

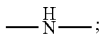

M is selected from:

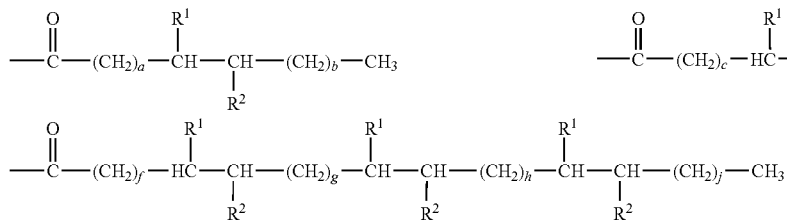

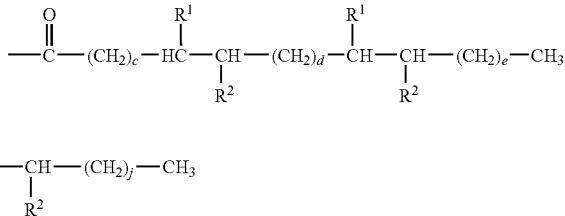

where —$R^1$ and —$R^2$ are selected from —OX, —OR, and —H, with the proviso that on vicinal carbon atoms:
one of —$R^1$ or —$R^2$ is —OX, and
one of —$R^1$ or —$R^2$ is —H;
or
one of —$R^1$ or —$R^2$ is —OX, and
one of —$R^1$ or —$R^2$ is —OR;
a, b, c, d, e, f, g, h, an j are independently selected integers;
X is H or M; and
R is a straight or branched chain alkyl group, for example, methyl, ethyl, propyl, butyl, and the like.

In exemplary embodiments, (a+b)=24; (c+d+e)=22; and (f+g+h+j)=20. In a preferred embodiment, a+b=14, (c+d+e)=12; and (f+g+h+j)=10.

In other exemplary embodiments of the invention Q is O; R is methyl; and p is 3 to 6.

Properties of the Polyester Polyol:

Polyester polyols of the invention typically have a number average hydroxyl functionality (Fn) that ranges from about 1.5 to about 10. Number average hydroxyl functionality refers to the average number of pendant hydroxyl groups (e.g., primary, secondary, or tertiary hydroxyl groups) that are present on a molecule of the polyester polyol. In some embodiments, the polyester polyols have a number average hydroxyl functionality (Fn) that ranges from about 2 to about 8. In some embodiments, the polyester polyols have a number average hydroxyl functionality (Fn) that ranges from about 2.5 to about 3.5. Polyols having a Fn ranging from about 2.5 to about 3.5 are desirable for use in flexible foams such as flexible slabstock foams. In some embodiments, the polyester polyol has a functionality of about 3.5 or greater, for example, about 3.5 to about 8. Polyester polyols with a Fn much greater than 3 may be useful, for example, in the production of rigid foams. In some embodiments, the polyester polyol has a Fn of about 2.5 or less, for example, about 1.5 to about 2.5. Polyester polyols having a Fn of about 2.5 or less may be useful, for example, in the formulation of polyurethane coatings, polyurethane adhesives, polyurethane sealants, and polyurethane elastomers.

In some embodiments, the polyester polyol has a hydroxyl number (OH number) that ranges from about 20 to about 500 mg KOH/g, or from about 25 to about 150 mg KOH/g. Hydroxyl number indicates the number of reactive hydroxyl groups available for reaction. It is expressed as the number of milligrams of potassium hydroxide equivalent to the hydroxyl content of one gram of the sample.

In some embodiments, the polyester polyol is a triol (i.e., Fn of 3) having a hydroxyl number in the range of about 28 mg KOH/g to about 60 mgKOH/g. Such triols are desirable because they may be used in the production of flexible polyurethane formulations where the polyester polyol replaces at least a portion of petroleum-derived triols that are typically used in such formulations. For example, in some embodiments, the polyester polyol replaces at least a portion of a petroleum-derived triol having a molecular weight of about 3000 grams/mole and a hydroxyl number of about 56 that is used in flexible slabstock formulations.

In some embodiments, the polyester polyol has a low acid value. Acid value is equal to the number of milligrams of potassium hydroxide (KOH) that is required to neutralize the acid that is present in one gram of a sample of the polyol (i.e., mg KOH/gram). A high acid value is undesirable because the acid may neutralize the amine catalyst causing a slowing of the foaming rate. In some embodiments, the polyester polyol has an acid value that is less than about 5 (mg KOH/gram), for example, less than about 4 (mg KOH/gram), less than about 3 (mg KOH/gram), less than about 2 (mg KOH/gram), or less than about 1 (mg KOH/gram). In exemplary embodiments, the acid value is less than about 1 (mg KOH/gram), for example, less than about 0.5 (mg KOH/gram), or from about 0.1 to about 0.5 (mg KOH/gram).

In some embodiments, the number average molecular weight (i.e, Mn) of the polyester polyol is about 1000 grams/mole or greater, for example, about 1100 grams/mole or greater, about 1200 grams/mole or greater, about 1300 grams/mole or greater, about 1400 grams/mole or greater, or about 1500 grams/mole or greater. In some embodiments, the Mn is less than about 10000 grams/mole, for example, less than about 6000 grams/mole, less than about 3000 grams/mole, or less than about 2000 grams/mole. In some embodiments, the Mn ranges from about 1000-10000 grams/mole, for example, about 1200-8000 grams/mole, about 1300-6000 grams/mole, about 1500-4000 grams/mole, or about 1800-3000 grams/mole. Number average molecular weight may be measured using gel permeation chromatography ("GPC") as described below.

Typically, the polyester polyols of the invention have a polydispersity (Mw/Mn) of about 1 to about 10, preferably 1 to 5, and most preferably 1 to 3.

Polyester polyols of the invention have a viscosity at 25° C. that typically ranges from about 0.5 to about 20 Pa·s, for example, from about 0.5 to about 10 Pa·s, or from about 0.5 to about 5 Pa·s.

In some embodiments, the polyester polyol has few, if any, residual double bonds. This is particularly true if the polyester polyol is prepared from a fully epoxidized natural oil or fatty acid ester. One measure of the amount of double bonds in a substance is its iodine value (IV). The iodine value for a compound is the amount of iodine that reacts with a sample of a substance, expressed in centigrams iodine ($I_2$) per gram of substance (cg $I_2$/gram). In some embodiments, the polyester polyol has an iodine value that is less than about 50, for example, less than about 40, less than about 30, less than about 20, less than about 10, or less than about 5.

Polymers

In another aspect the invention provides polymers (e.g., polyesters, polyurethanes, and polycarbonates) that are prepared from the polyester polyols of the invention.

In an exemplary embodiment, the polymers are polyurethanes that comprise the reaction product of (a) a polyisocyanate; and (b) a polyester polyol of the invention.

Foams

Polyester polyols of the invention are useful in the preparation of polyurethanes, for example, slabstock polyurethane foams or molded polyurethane foams. In some embodiments, the polyurethane foam comprises the reaction product of: (a) a polyisocyanate; and (b) an active-hydrogen containing composition comprising a polyester polyol of the invention.

The hydroxyl groups of the polyester polyol chemically reacts with the isocyanate groups of the polyisocyanate to form the urethane linkages in the resulting polyurethane foam. Thus, the polyester polyol is chemically incorporated into the polyurethane polymer.

The amount of polyester polyol included in the active hydrogen-containing composition may be selected based upon the desired performance of the foam. For example, in some embodiments, the active-hydrogen containing composition may comprise from about 10% to about 100% weight of the polyester polyol, for example, about 10% to about 60% weight polyester polyol, or about 15% to about 40% weight polyester polyol.

In some embodiments, the active-hydrogen containing composition comprises an polyester polyol and a petroleum-derived polyol. For example, in some embodiments, the active-hydrogen containing composition comprises about 10% to about 90% weight polyester polyol and about 10% to about 90% weight petroleum-derived polyol. In some embodiments, the active-hydrogen containing composition comprises about 10% to about 60% weight polyester polyol and about 40% to about 90% weight petroleum-derived polyol. In other embodiments, the active-hydrogen containing composition comprises about 15% to about 40% weight polyester polyol and about 60% to about 85% weight petroleum-derived polyol.

In some embodiments, the polyurethane foam is a flexible foam and the petroleum-derived polyol is a triol, for example, having an average of about 2.7 to about 3.1 hydroxyl groups per molecule. In a specific embodiment, the triol has a weight average molecular weight (Mw) of about 3000 grams/mole to about 3500 grams/mole. Representative examples of commercially available petroleum-derived triols include those available under the trade designations ARCOL F3040, ARCOL F3022, and ARCOL 3222 (from Bayer), PLURACOL 1385 and PLURACOL 1388 (from BASF), VORANOL 3322, VORANOL 3010, VORANOL 3136, and VORANOL 3512A (from Dow).

In other embodiments, the polyurethane foam is a molded foam and the molecular weigh of the polyol ranges from about 3000 to about 6000 grams/mole. Representative examples of commercially available petroleum-derived polyols for use in molded foams include VORANOL 6340 (from Dow) and MULTRANOL 3901 (from Bayer).

Polyisocyanates

Representative examples of useful polyisocyanates include those having an average of at least about 2.0 isocyanate groups per molecule. Both aliphatic and aromatic polyisocyanates can be used. Examples of suitable aliphatic polyisocyanates include 1,4-tetramethylene diisocyanate, 1,6-hexamethylene diisocyanate, 1,12-dodecane diisocyanate, cyclobutane-1,3-diisocyanate, cyclohexane-1,3- and 1,4-diisocyanate, 1,5-diisocyanato-3,3,5-trimethylcyclohexane, hydrogenated 2,4- and/or 4,4'-diphenylmethane diisocyanate ($H_{12}$MDI), isophorone diisocyanate, and the like. Examples of suitable aromatic polyisocyanates include 2,4-toluene diisocyanate (TDI), 2,6-toluene diisocyanate (TDI), and blends thereof, 1,3- and 1,4-phenylene diisocyanate, 4,4'-diphenylmethane diisocyanate (including mixtures thereof with minor quantities of the 2,4'-isomer) (MDI), 1,5-naphthylene diisocyanate, triphenylmethane-4,4',4"-triisocyanate, polyphenylpolymethylene polyisocyanates (PMDI), and the like. Derivatives and prepolymers of the foregoing polyisocyanates, such as those containing urethane, carbodiimide, allophanate, isocyanurate, acylated urea, biuret, ester, and similar groups, may be used as well.

The amount of polyisocyanate preferably is sufficient to provide an isocyanate index of about 60 to about 120, preferably about 70 to about 110, and, in the case of high water formulations (i.e., formulations containing at least about 5 parts by weight water per 100 parts by weight of other active hydrogen-containing materials in the formulation), from about 70 to about 90. As used herein the term "isocyanate index" refers to a measure of the stoichiometric balance between the equivalents of isocyanate used to the total equivalents of water, polyols and other reactants. An index of 100 means enough isocyanate is provided to react with all compounds containing active hydrogen atoms.

Polyurethane Catalysts

Examples of useful polyurethane catalysts include tertiary amine compounds and organometallic compounds. Specific examples of useful tertiary amine compounds include triethylenediamine, N-methylmorpholine, N-ethylmorpholine, diethyl ethanolamine, N-coco morpholine, 1-methyl-4-dimethylaminoethyl piperazine, 3-methoxy-N-dimethylpropylamine, N,N-diethyl-3-diethylaminopropylamine, dimethylbenzyl amine, bis(2-dimethylaminoethyl)ether, and the like. Tertiary amine catalysts are advantageously used in an amount from about 0.01 to about 5, preferably from about 0.05 to about 2 parts per 100 parts by weight of the active hydrogen-containing materials in the formulation.

Specific examples of useful organometallic catalysts include organic salts of metals such as tin, bismuth, iron, zinc, and the like, with the organotin catalysts being preferred. Suitable organotin catalysts include dimethyltindilaurate, dibutyltindilaurate, stannous octoate, and the like. Other suitable catalysts are taught, for example, in U.S. Pat. No. 2,846,408, which is hereby incorporated by reference. Preferably, about 0.001 to about 1.0 parts by weight of an organometallic catalyst is used per 100 parts by weight of the active hydrogen-containing materials in the formulation. Blends of catalysts may also be used.

Blowing Agents

The blowing agent generates a gas under the conditions of the reaction between the active hydrogen compound and the polyisocyanate. Suitable blowing agents include water, liquid carbon dioxide, acetone, methylene chloride, and pentane, with water being preferred.

The blowing agent is used in an amount sufficient to provide the desired foam density and IFD. For example, when water is used as the only blowing agent, from about 0.5 to about 10, preferably from about 1 to about 8, more preferably from about 2 to about 6 parts by weight, are used per 100 parts by weight of other active hydrogen-containing materials in the formulation.

Other Additives

Other additives that may be included in the formulation include surfactants, catalysts, cell size control agents, cell opening agents, colorants, antioxidants, preservatives, static dissipative agents, plasticizers, crosslinking agents, flame retardants, and the like.

Examples of useful surfactants include silicone surfactants and the alkali metal salts of fatty acids. The silicone surfactants, e.g., block copolymers of an alkylene oxide and a dimethylsiloxane, are preferred, with "low fog" grades of silicone surfactants being particularly preferred.

In some cases, a static dissipative agent may be included in the formulation during foam preparation, or used to treat the finished foam. Useful examples include non-volatile, ionizable metal salts, optionally in conjunction with an enhancer compound, as described in U.S. Pat. Nos. 4,806,571, 4,618,630, and 4,617,325. Of particular interest is the use of up to about 3 weight percent of sodium tetraphenylboron or a sodium salt of a perfluorinated aliphatic carboxylic acid having up to about 8 carbon atoms.

Manufacturing of Polyurethane Foams

Polyurethane foams of the invention can be manufactured using known techniques for producing conventional slabstock (i.e., free-rise) and molded foams. In slabstock processes, the polyurethane reactants are mixed together and are poured onto a conveyor where the reacting mixture rises against its own weight and cures to form a slabstock bun having a nominal rectangular cross-section. The resulting slabstock bun can be cut into the desired shape to suit the end-use. In a molded foam process the reactants are mixed and dispensed into a mold where they react to fill the mold and assume the shape of the mold cavity. After the molded foam is cured, the mold is opened and the molded polyurethane article is removed.

Slabstock polyurethane foams can be manufactured using conventional slabstock foaming equipment, for example, commercial box-foamers, high or low pressure continuous foam machines, crowned block process, rectangular block process (e.g., Draka, Petzetakis, Hennecke, Planiblock, EconoFoam, and Maxfoam processes), or verti-foam process. In some embodiments, the slabstock foam is produced under reduced pressure. For example, in variable pressure foaming (VPF), the complete conveyor section of the foaming machine is provided in an airtight enclosure. This technique allows for the control of foam density and the production of foam grades that may otherwise be difficult to produce.

Details of such slabstock foaming processes are reported, for example, in Chapter 5 of *Flexible Polyurethane Foams*, edited by Herrington and Hock, (2$^{nd}$ Edition, 1997, Dow Chemical Company).

In some instances, it is desirable to post-cure the foam after initial forming (and demolding in the case of molded foam) to develop optimal physical properties. Post-curing may take place under ambient conditions, for example, for a period of about 12 hours to 7 days; or at elevated temperature, for example, for a period of about 10 minutes to several hours.

The foams can be used in a variety of applications, for example, they may be incorporated into seat components (e.g. seat cushions, seat backs, arm rests, and the like) for use in motor vehicles, bedding (mattresses) or furniture.

The invention will be further illustrated with reference to the following examples which are intended to aid in the understanding of the present invention, but which are not to be construed as a limitation thereof.

EXAMPLES

Materials

Soybean Oil, Canola Oil, and High Oleic Sunflower Oil (>80% units derived from oleic acid), available from Cargill, Inc.

Partially hydrogenated soybean oil: 693 SBO from Cargill, Inc. The partially hydrogenated soybean oil has an Iodine value of 74.6 and contains 18.9% saturated fatty acids, 70.1% monounsaturated fatty acids, and 3.5% polyunsaturated fatty acids.

Methanol: anhydrous grade, from EMD Chemicals
Sodium methoxide: 95% powder, from Sigma-Aldrich
Hydrogen peroxide, 30% solution, from VWR international
Glacial Acetic Acid, from EMD Chemicals
Toluene, 99.5%, from EMD Chemicals
Amberlite-IR-120H, ion-exchange resin, from Sigma-Aldrich
Fluoroboric Acid, 48% aqueous solution, from EMD Chemicals
Lewatit-64, ion-exchange resin, from Sybron
Trimethylolpropane (TMP), from POLIOLI.S.P.A
FASCAT (R)-4350, from ATOFINA.
Titanium tetraisopropoxide, from Sigma-Aldrich
Natural Oil Polyol 1 ("NOP-1") is made by ring opening epoxidized soybean oil with MeOH.
NOP-1 has a hydroxyl number of about 180 mg KOH/gram; a viscosity of about 5000 cps @ 25° C.; and a Mn of about 1100.
Natural Oil Polyol 2 ("NOP-2") is made by ring opening epoxidized soybean oil with a MeOH/H$_2$O mixture. NOP-2 has a hydroxyl number of about 235 mg KOH/gram; a viscosity of about 8900 cp @ 25° C.; and a Mn of about 1100.

Test Procedures

Hydroxyl Value (OH Value) was measured using ASTM E 1899-97, except that a mixture of 50% acetonitrile and 50% toluene is used as the solvent.
Acid Value is measured according to IUPAC method 2.201.
Epoxide oxygen content (EOC) is measured using AOCS Cd9-57 method.
Viscosity is measured using a AR 2000ex Rheometer available from TA Instruments. The measurement conditions were as follows: gap distance of 55 μm, cone type plate, 40 mm plate diameter, 2 degree plate angle, and temperature of 25° C.

Number average molecular weight (Mn) is measured by GPC on a Waters system, with 5 columns in series. The columns were Phenogel 5-50A 300×7.8 mm, 5-100A 300×7.8 mm, 5-10$^3$A 300×7.8 mm, 5-10$^4$A 300×7.8 mm, and 5-Linear/Mixed, 50×7.8 mm. A temperature of 30° C. and flow rate of 1 ml/minutes were used. The following materials were used as molecular weight standards: Arcol LHT-240 (MW 700), Soybean oil (MW 874), Epoxidized soybean oil (MW 940), Acclaim 2200 (MW 2008), Multranol 3400 (MW 3000) and Acclaim 8200 (MW 7685).

Example 1

Preparation of Polyester Polyol of from High Oleic Sunflower Oil (HOSFO)

Step 1: Methanolysis of High Oleic Sunflower Oil
Methanolysis was carried out by refluxing a mixture containing methanol (43.2 parts) and high oleic sunflower oil (HOSFO, 100 parts). The molar ratio of methanol to ester bonds was 4:1. 0.3 wt % of sodium methoxide (0.43 parts) was used as catalyst for the reaction. The reaction took approximately 4 hours to reach completion. The product was then washed with water in order to remove the base catalyst and the glycerol generated during the reaction. The fatty acid methyl ester (FAME) was dried at 80° C. under high vacuum (<1 Torr).

Step 2: Epoxidation of FAMEs from HOSFO
100 parts of FAME from Step 1 was epoxidized using 30% hydrogen peroxide (59.89 parts), catalyzed with Amberlite IR-120 (7.14 parts) and acetic acid (10.57 parts). Toluene (42.86 parts) was added in order to improve the miscibility between the FAMEs and the hydrogen peroxide. The epoxidation was carried out at 70° C. for 7 hours. The product was washed multiple times with water until the pH of the aqueous phase was about 7. The epoxidized FAMEs was then dried at 80° C. under high vacuum (<1 Torr).

Step 3: Reaction of Epoxidized FAMEs with Methanol
100 parts of epoxidized FAME from Step 2 was ring-opened with 100.39 parts methanol. The molar ratio of methanol to epoxide groups was 10:1. The ring-opening reaction was catalyzed with 0.02 wt % of HBF$_4$ (0.08 parts), and carried out under refluxing conditions at 65-70° C. for 30-35 minutes. The excess methanol was then distilled off at 80° C. under high vacuum (<1 Torr). The resulting product was a light yellow, low viscous liquid. The properties of the product are shown in TABLE 1-1.

TABLE 1-1

| Property | Value |
| --- | --- |
| Hydroxyl Number | 155 mg KOH/g |
| Acid Value | 1.12 mg KOH/g |
| Functionality | 0.97 |
| Equivalent Weight | 362 |

Step 4: Polyol Synthesis from Hydroxylated High Oleic Sunflower Oil FAMEs
Hydroxylated fatty acid methyl esters, TMP, and Fascat (R)-4350 catalyst in the amounts shown in TABLE 1-2 were placed in a flask that was equipped with a heating mantle, thermocouple, heat controller, and distillation condenser attached to a vacuum pump. The mixture was heated to 220° C. The TMP and Fascat melted and dissolved completely at about 150° C., and the reaction mixture became clear. The first drops of methanol from the transesterification reaction began to distill over at about 190° C. The reaction mixture was maintained at 220° C. for 3 hours. A vacuum (~50 torr) was applied and held for about 1 hour, and the vacuum was then increased to <8 torr and held for 3-4 hours. As the amount of methanol being distilled became very low, the vacuum decreased to 1-2 torr. The product was then allowed to cool to room temperature. The resulting polyols had the properties listed in TABLE 1-3.

TABLE 1-2

| | Hydroxylated FAMEs (parts) | Initiator (parts) | Catalyst (parts) |
|---|---|---|---|
| Polyol 1.1 | 100 | TMP (4.12) | 1.04 |
| Polyol 1.2 | 100 | NOP-1 (13.98) | 0.57 |

TABLE 1-3

| | OH# (mg KOH/g) | Acid # (mg KOH/Kg) | Mn | Mw | Fn | Fw | Mw/Mn | Viscosity (Pa·s) |
|---|---|---|---|---|---|---|---|---|
| Polyol 1.1 | 49 | 1.51 | 2004 | 4261 | 1.75 | 3.72 | 2.13 | 7.0 |
| Polyol 1.2 | 36 | 0.91 | 1699 | 4930 | 1.09 | 3.15 | 2.9 | 5.8 |

Example 2

Synthesis of Polyols from Soy, Canola and Sunflower Oils

Step 1: Methanolysis High-Oleic Sunflower, Soy and Canola Oils

The methanolysis of high-oleic sunflower oil (HOSFO) was carried out by boiling a mixture of methanol (218 parts) and HOSFO (100 parts) in a molar ratio of methanol to ester bonds of 20:1. Sodium methoxide (3.18 parts) was used as the catalyst. The reaction was complete in approximately 3 hours. The product was cooled to room temperature, and after separating the methanol/glycerol phase, the product was washed multiple times with water to remove residual catalyst and glycerol. The FAME was then dried on a rotary evaporator at 80° C. under high vacuum (<1 mm Hg) for 1-2 hours. Similar procedures using Soybean oil and Canola oil provided methyl esters (FAMEs) of their corresponding fatty acid mixtures.

Step 2: Epoxidation of FAMEs from Soy, Canola and High Oleic Sunflower Oil

The FAMEs from Step 1 were epoxidized using hydrogen peroxide and glacial acetic acid, catalyzed by Amberlite-IR-120H as described above. Toluene was added in order to improve the miscibility between the FAME and hydrogen peroxide. The epoxidation was carried out at 80° C. for 6 hours. The products were washed with water until the aqueous phase had a pH of about 7. The epoxidized FAMEs were then dried on a rotary evaporator at 80° C. under high vacuum (<1 mm Hg) for 1-2 hours. TABLE 2-1 details the quantities of reagents used in the epoxidation reaction.

TABLE 2-1

| Type of FAME | Quantity of FAME (parts) | Quantity of Acetic acid (parts) | Quantity of Amberlite 120H (parts) | Quantity of 30% H2O2 (parts) | Quantity of Toluene (parts) |
|---|---|---|---|---|---|
| Soy | 100 | 20 | 30 | 100 | 150 |
| Canola | 100 | 100 | 20 | 100 | 200 |
| High-Oleic Sunflower | 100 | 12.1 | 19.7 | 65.8 | 51 |

Step 3: Synthesis of Hydroxylated FAMEs

The epoxy rings in the epoxidized FAMEs of Step 2 were ring-opened by reaction with methanol. A molar ratio of methanol to epoxy ring of 9:1 was used. The reactions were carried out under refluxing conditions at 65-70° C. for 30-35 minutes. HBF4 was used as the ring-opening catalyst. After ring-opening the catalyst was neutralized with Lewatit-64. The excess methanol was removed on rotary evaporator at 70° C. under high vacuum (<1 mm Hg) for about 1 hour. The amounts of the reactants are listed in TABLE 2-2. The properties of the resulting ring-opened compounds are shown in TABLE 2-3.

TABLE 2-2

| Type Of Epoxidized FAME | EOC (%) | Quantity of Epoxidized FAME (parts) | Quantity of MeOH (parts) | Quantity of 48% Fluoroboric acid (parts) |
|---|---|---|---|---|
| Soy | 7.01 | 100 | 126 | 0.24 |
| Canola | 5.72 | 100 | 103 | 0.43 |
| HOSFO | 4.70 | 100 | 85 | 0.39 |

TABLE 2-3

| Type of FAME | OH# (mg KOH/g) | Equivalent Weight |
|---|---|---|
| Soy | 171 | 328 |
| Canola | 165 | 339 |
| HOSFO | 160 | 351 |

Step 4: Polymerization of Hydroxylated Fatty Acid Methyl Esters to Polyols

The polymerization conditions were similar to the reaction conditions used for the polymerization of hydroxylated FAME in Example 1. A mixture of the hydroxylated fatty acid methyl esters, initiator, and catalyst were heated at 220° C. for 3 hours without applying a vacuum, followed by heating at 220° C. under medium vacuum (50-100 mm Hg) for 1 hour. Finally, the mixture was heated at 220° C. under high vacuum (1-2 mm Hg) for 2-3 hours. The polymerization was catalyzed by 1 wt % of Fascat(R)-4350.

The polymerization of hydroxylated FAMEs made from HOSFO was initiated with TMP using a molar ratio of hydroxylated FAMEs to TMP of 9:1. Because the hydroxylated FAMEs made from soybean oil and canola oil contained a higher percentage of difunctional and trifunctional hydroxylated FAMEs, the polymerization reaction of these hydroxylated FAMEs was initiated with a mixture of TMP and ethylene glycol (EG) in order to limit the functionality of the final polyols. The polymerization of soybean oil-based hydroxylated FAMEs was initiated using a mixture of TMP and EG in a molar ratio of TMP to EG of 1:1.28. The molar ratio of hydroxylated FAMEs to initiators in this reaction was 9:1. The polymerization of canola oil-based hydroxylated FAMEs was initiated by a mixture of TMP and EG in a molar ratio of TMP to EG of 1:0.85. The molar ratio of hydroxylated FAMEs to initiators in this reaction was also 9:1. The amount of reactants are shown in TABLE 2-4. The properties of the resulting polyester polyols are shown in TABLE 2-5.

TABLE 2-4

| Type of FAME | Polyol | Quantity of Hydroxylated FAME (parts) | Quantity of TMP (parts) | Quantity of Ethylene glycol (parts) | Quantity of Fascat (R)-4350 (parts) |
|---|---|---|---|---|---|
| Soy | 2.1 | 100 | 1.8 | 1.06 | 1.03 |
| Canola | 2.2 | 100 | 2.25 | 0.89 | 1.03 |
| HOSFO | 2.3 | 100 | 4.24 | — | 1.04 |

TABLE 2-5

| Polyol | OH# (mg KOH/g) | Acid # (mg KOH/Kg) | Mn | Mw | Fn | Fw | Mw/Mn | Viscosity (Pa·s) |
|---|---|---|---|---|---|---|---|---|
| 2.1 | 51.7 | 2.93 | 2274 | 20063 | 2.09 | 18.48 | 8.82 | gel |
| 2.2 | 53.5 | 3.65 | 2018 | 8234 | 1.92 | 7.84 | 4.08 | 29.7 |
| 2.3 | 50.8 | 1.97 | 2101 | 5236 | 1.9 | 4.74 | 2.49 | 8.6 |

Ingredient List for Polyurethane Foams:
ARCOL F-3022—a petroleum-derived, nominal 3000 molecular weight triol having a hydroxyl number of 54.3 mg KOH/g and an acid number of 0.03 mg KOH/gram (commercially available under the trade designation "ARCOL F-3022" from Bayer).
Amine BL11—a blowing catalyst consisting of 70% bis(dimethylaminoethyl)ether and 30% dipropylene glycol (commercially available under the trade designation "DABCO BL-11" from Air Products).
Tin K29—stannous octoate catalyst (commercially available from Degussa).
Silicone EP-H-140—silicone surfactant.
TDI—toluene diisocyanate.

A foam comprising polyester polyol 2.3 was prepared and tested as described below.

First, a 400 ml plastic beaker was positioned on an electric scale. Next, the formulation required amount of polyol(s) were added to the beaker. Next, the formulation required amount of silicone surfactant and amine catalyst were added to the beaker. Next, the formulation required amount of tin catalyst and water were added to the batch. The temperature of the B-side was adjusted so that upon mixing with the polyisocyanate the combined mixture had a temperature of 19.2°±0.3° C. The batch was mixed with an electric, lab duty mixer (Delta ShopMaster brand, Model DP-200, 10 inch shop drill press) equipped with a 2" diameter mixing blade (ConnBlade Brand, Model ITC from Conn Mixers Co.) for 19 seconds at 2340 rpm.

Separately, the formulation required amount of TDI was weighed out into a 50 ml plastic beaker and was set near the mixing station. The TDI was then added to the polyol mixture and was mixed for 6 seconds. Following this, the mixture was poured into an 83 ounce cup and was allowed to free rise. During the free rise period, the Cream Time (i.e., the time from the introduction of the TDI until start of cream rise in the cup), Top of Cup Rise Time (i.e., the time from the introduction of the TDI until the dome of the foam reaches the top of the cup), and the Total Rise Time (i.e., the time from the introduction of the TDI until there is blow-off or no more rising of the foam) were each recorded. The foam and cup were then placed into a temperature-controlled oven at 100° C. for 15 minutes to cure. At the end of the oven cure, the foam was permitted to cure overnight. After curing overnight, the foam was conditioned for 72 hours at 25° C. and 50% relative humidity before testing for physical properties. The physical property test results are reported in TABLE 2-6.

TABLE 2-6

| Arcol F-3022 | | 100 | 70 |
|---|---|---|---|
| Polyol 2.3 | | 0 | 30 |
| Water (pph) | | 3.949 | 3.949 |
| Silicone (pph) | EP-H-140 | 1 | 1 |
| Amine (pph) | BL-11 | 0.16 | 0.16 |
| Tin (pph) | K-29 | 0.23 | 0.23 |
| TDI Index | | 105 | 105 |
| Foam properties | | | |
| Density (pcf) | | 1.5 | 1.47 |
| Resiliency (%) | | 40.67 | 35.5 |
| 25% IFD (N) | | 23.83 | 27.28 |
| 65% IFD (N) | | 42.34 | 45.99 |
| Support Factor | | 1.78 | 1.69 |
| IFD (15 × 15 × 4) (lbs/50 sq. in.) | | 29.65 | 33.94 |
| Tensile (kPa) | | 120.91 | 117.75 |
| Elongation (%) | | 226.21 | 188.19 |
| Tear (N/m) | | 521.25 | 376.25 |
| Permeability (cfm) | | 3.64 | 3.6 |
| 90% CS (% loss) | | 25.7 | 12.83 |

Example 3

Polyester Polyols Prepared from Partially Hydrogenated Soybean Oil

Step 1: Methanolysis of Partially Hydrogenated Soybean Oil

Partially hydrogenated soybean oil (from Cargill) having an iodine value of 74.6, was used in this reaction. Methanolysis was carried out by refluxing a mixture of methanol (43.64 parts) and partially hydrogenated soybean oil (100 parts) in a molar ratio of methanol to ester bonds of 4:1. Sodium methoxide (0.50 parts) was used as the catalyst. The reaction needed about 4 hours for completion. The product was then washed with water to remove the base catalyst, and the glycerol generated during the reaction. The FAMEs were then dried on a rotary evaporator at 80° C. under high vacuum (<1 mm Hg) for a few hours.

Step 2: Epoxidation of FAMEs from Partially Hydrogenated Soybean Oil

FAMEs (100 parts) from Step 1 were epoxidized using 30% hydrogen peroxide (59.9 parts) and glacial acetic acid (10.58 parts), catalyzed by Amberlite-IR-120H (7.15 parts). Toluene (42.88 parts) was added in order to improve the miscibility between the FAME and hydrogen peroxide. The reaction was carried out at 80° C. for 6 hours. The product was then washed with water until the pH of the aqueous phase was about 7. The epoxidized FAMEs were then dried on a rotary evaporator at 80° C. under high vacuum (<1 mm Hg) for a few hours. The product had an EOC of 3.82%.

Step 3: Ring Opening of Epoxidized FAMEs from Partially Hydrogenated Soybean Oil The mixture of epoxidized FAMEs (100 parts) from Step 2 was reacted with methanol (68.77 parts) in a molar ratio of methanol to epoxy ring of 9:1. The mixture was catalyzed by 0.05 wt % fluoroboric acid (0.18 parts), and the reaction carried out under refluxing conditions (65-70° C.) for 30-35 minutes. The excess methanol was then removed on a rotary evaporator at 70° C. under high vacuum (<1 mm Hg) for 1 hour. The hydroxylated FAMEs had a OH# of 137 mgKOH/g.

Step 4: Polymerization of Hydroxylated FAMEs from Partially Hydrogenated Soybean Oil The polymerization was carried out at 220° C., as described above for the other polyols, catalyzed by 0.5 wt % of Fascat (R)-4350. The initial stages of the polymerization was carried out at 220° C. for 3 hours without a vacuum, followed by 220° C. under medium vacuum (50-100 mm Hg) for 1 hour, and finally at 220° C. under high vacuum (1-2 mm Hg) for 2-3 hours. The reaction was usually complete by the time the pressure in the flask dropped to <1 Torr. The products were low viscous, clear liquids with a light yellow color. The quantities of FAME, TMP, X-210, and Fascat 4350 are shown in TABLE 3-1. The properties of the resulting polyols are shown in TABLE 3-2.

TABLE 3-1

| Polyol | Quantity of Hydroxylated FAMEs (parts) | Quantity of TMP (parts) | Quantity of NOP-2 (parts) | Quantity of Fascat (R)-4350 (parts) |
|---|---|---|---|---|
| 3.1 | 100 | 4.43 | — | 0.52 |
| 3.2 | 100 | 2.21 | 28.93 | 0.66 |
| 3.3 | 100 | — | 57.54 | 0.79 |
| 3.4 | 100 | — | 86.3 | 0.94 |
| 3.5 | 100 | 6.65 | 0 | 0.53 |
| 3.6 | 100 | 3.33 | 43.15 | 0.73 |

TABLE 3-2

| | OH# (mg KOH/g) | Acid # (mg KOH/Kg) | Mn | Mw | Fn | Fw | Mw/Mn | Viscosity (Pa·s) |
|---|---|---|---|---|---|---|---|---|
| 3.1 | 34 | 1.06 | 1732 | 2898 | 1.06 | 1.77 | 1.67 | 2.8 |
| 3.2 | 46 | 0.71 | 1875 | 3625 | 1.53 | 2.95 | 1.93 | 5.3 |
| 3.3 | 50 | 0.55 | 2139 | 5609 | 1.92 | 5.03 | 2.62 | 10.8 |
| 3.4 | 73 | 0.97 | 1889 | 5101 | 2.45 | 6.62 | 2.70 | 11.8 |
| 3.5 | 55 | 0.77 | 1415 | 2479 | 1.38 | 2.41 | 1.75 | 2.3 |
| 3.6 | 74 | 0.96 | 1513 | 3365 | 1.99 | 4.45 | 2.22 | 4.9 |

Example 4

Comparison of Fascat (R)-4350 Versus Titanium Tetraisopropoxide

The ingredients shown in TABLE 4-1 were reacted at 220° C. without vacuum for two hours. The methanol that was distilled off was collected and the amount recorded. The extent of reaction was determined based on the amount of methanol that was collected. After the first 2 hours at 220° C., a medium vacuum (50-100 mm Hg) was applied for an additional two hours. Then, a high vacuum (1-2 mm Hg) was applied, and the time needed for each reaction to go to completion was recorded.

The extent and efficiency of the polymerization reaction was determined by the following methods:

1. The quantity of methanol generated during the first two hours of the reaction, when no vacuum was applied.
2. The number average molecular weight (Mn) of the reaction mixture.
3. The amount of monomer (hydroxylated FAME) remaining (by GPC).
4. The hydroxyl value of the reaction mixture.

The results are recorded in TABLE 4-2

TABLE 4-1

| | Polyol | |
|---|---|---|
| | 4.1 | 4.2 |
| Hydroxyl functional FAMEs from High Oleic Sunflower Oil | 100 | 100 |
| TMP | 4.12 | 4.12 |
| Fascat 4350 | 1.04 | 0 |
| Titanium tetraisopropoxide | 0 | 1.04 |

TABLE 4-2

| | Catalyzed by FASCAT | Catalyzed by Ti-Isopropoxide |
|---|---|---|
| Conversion after 2 hours heating without vacuum (%) | 62.6 | 38.8 |
| Mn reached after 2 hours under high vacuum | 2295 | 1652 |
| Monomer remaining after 2 hours under high vacuum (%) | 1.96 | 4.27 |
| Hydroxyl value after 2 hours under high vacuum (mg KOH/g) | 48.42 | 60.33 |
| Mn reached after 3 hours under high vacuum | Finished | 2208 |
| Monomer remaining after 3 hours under high vacuum (%) | Finished | 2.34 |
| Hydroxyl value after 3 hours under high vacuum (mg KOH/g) | Finished | 50.24 |

Example 5

Effect of Catalyst Concentration on the Reaction

Hydroxylated FAME from high oleic sunflower oil (100 parts), TMP (4.12 parts) and Fascat (R)-4350 were used for this example. Five catalyst concentrations were studied: 1 wt %, 0.75 wt %, 0.5 wt %, 0.25 wt % and 0.1 wt %. The reactions were carried out at 220° C. for two hours without a vacuum, then at the same temperature for 30 minutes under slight vacuum (50-100 Mm Hg). Finally, the reaction was conducted for 30 minutes under high vacuum (1-2 Mm Hg) until the pressure dropped to less than 1 Torr. The quantity of methanol collected after two hours without vacuum was recorded and was used to calculate the extent of reaction. The reaction time needed to complete the reactions was also recorded. The results are shown in TABLE 5-1.

TABLE 5-1

| ID Number | 5.1 | 5.2 | 5.3 | 5.4 | 5.5 |
|---|---|---|---|---|---|
| Quantity of catalyst (wt. %) | 1 | 0.75 | 0.5 | 0.25 | 0.1 |
| Conversion after 2 hours heating under high vacuum (%) | 62.6 | 59.8 | 52.2 | 42.3 | 29.2 |

TABLE 5-1-continued

| ID Number | 5.1 | 5.2 | 5.3 | 5.4 | 5.5 |
|---|---|---|---|---|---|
| OH number after 2 hours heating under high vacuum (mg KOH/g) | 48.42 | 49.24 | 58.82 | NA | NA |
| OH number after 4 hours heating under high vacuum (mg KOH/g) | Finished | Finished | 48.73 | 57.82 | NA |
| OH number after 5 hours heating under high vacuum (mg KOH/g) | Finished | Finished | Finished | NA | 85.39 |
| OH number after 6 hours heating under high vacuum (mg KOH/g) | Finished | Finished | Finished | 53.83 | NA |
| OH number after 7 hours heating under high vacuum (mg KOH/g) | Finished | Finished | Finished | 49.5 | NA |
| OH number after 10 hours heating under high vacuum (mg KOH/g) | Finished | Finished | Finished | Finished | 61.43 |
| OH number after 15 hours heating under high vacuum (mg KOH/g) | Finished | Finished | Finished | Finished | 49.3 |
| OH number after 16 hours heating under high vacuum (mg KOH/g) | Finished | Finished | Finished | Finished | 48.42 |
| No. of hours under high vacuum to reach OH number of 48-50 mg KOH/g | 2 | 2 | 4 | 7 | 15 |
| No. of hours under high vacuum to reach monomer below 2% | 2 | 2 | 4 | 7 | 15 |
| No. of hours under high vacuum to reach Mn above 2200 | 2 | 2 | 4 | 7 | 15 |
| Final amount of cyclic compounds (%) | 3.7 | 3.5 | 3.8 | 4 | 3.7 |

Example 6

Effect of Temperature on the Polymerization Reaction

All polymerization reactions in this study were catalyzed using 0.5 wt % of Fascat. (R)-4350. Three different reaction temperatures, 220° C., 200° C. and 180° C., were studied. The amounts of hydroxylated FAME from sunflower oil and TMP were 100 parts and 4.12 parts respectively. The results are shown in TABLE 6-1.

TABLE 6-1

| | Polyol | | |
|---|---|---|---|
| | 6.1 | 6.2 | 6.3 |
| Quantity of catalyst (FASTCAT) (wt. %) | 0.5 | 0.5 | 0.5 |
| Reaction Temp (° C.) | 220 | 200 | 180 |
| Conversion after 2 hours heating without vacuum (%) | 52.2 | 36.2 | 19.3 |
| No of hours needed under high vacuum to reach OH number of 48-50 mg KOH/g | 4 | 6 | 13 |
| No of hours needed under high vacuum to reach monomer % below 2% | 4 | 6 | 13 |
| No of hours needed under high vacuum to reach Mn of above 2200 | 4 | 6 | 13 |
| Final amount of cyclic compounds (%) | 3.8 | 3.9 | 3.8 |

Example 7

Effect of Reaction Time on the Polymerization Reaction

This study was performed to extend the polymerization reaction time beyond its normal completion, and to determine how this would affect the properties of the product. The reaction was performed as in the previous experiment, but allowed to run for a long time. Samples were taken periodically and analyzed by GPC and OH# measurement. The results are shown in TABLE 7-1.

TABLE 7-1

| Sample ID | Number of hours heated under high vacuum | Hydroxyl value (mg KOH/g) | Remaining monomer (%) | Mn |
|---|---|---|---|---|
| 7.1 | 4 | 86 | 12.21 | 1009 |
| 7.2 | 6 | 73 | 7.92 | 1226 |
| 7.3 | 10 | 57 | 3.09 | 1805 |
| 7.4 | 13 | 50 | 2.31 | 2134 |
| 7.5 | 15 | 47 | 1.63 | 2389 |
| 7.6 | 17 | 45 | 1.49 | 2574 |
| 7.7 | 19 | 44 | 1.17 | 2707 |
| 7.8 | 20 | 43 | 1.05 | 2775 |

When the polymerization of the hydroxylated FAME was catalyzed by 0.5 wt % of Fascat at 180° C., it took ~13 hours under high vacuum for the reaction to reach the target OH# of ~50 and Mn of ~2200. As the reaction mixture is heated beyond this, the product begins to lose hydroxyl groups slowly, most likely due to side reactions.

OH#, remaining monomer, and Mn were recorded at various times when heated at 220° C. under high vacuum. The results are reported in TABLE 7-2.

TABLE 7-2

| Sample ID | Number of hours heated under high vacuum | Hydroxyl value (mg KOH/g) | Remaining monomer (%) | Mn |
|---|---|---|---|---|
| 7.9 | 3 | 55 | 2.69 | 1954 |
| 7.10 | 4 | 48 | 1.30 | 2319 |
| 7.11 | 5 | 44 | 1.54 | 2458 |
| 7.12 | 6 | 41 | 0.97 | 2644 |
| 7.13 | 7 | 39 | 0.87 | 2740 |
| 7.14 | 8 | 38 | 1.24 | 2834 |
| 7.15 | 10 | 36 | 0.56 | 2980 |

TABLE 7-2-continued

| Sample ID | Number of hours heated under high vacuum | Hydroxyl value (mg KOH/g) | Remaining monomer (%) | Mn |
|---|---|---|---|---|
| 7.16 | 12 | 34 | 0.44 | 3125 |
| 7.17 | 13 | 32 | 0.29 | 3296 |

The reaction at 180° C. lost about 1 OH# per hour, while the reaction at 220° C. lost about 2 OH#s per hour.

Example 8

Synthesis of Polyols from Epoxidized Partially Hydrogenated Soybean Oil

Step 1: Methanolysis of Partially Hydrogenated Soybean Oil

A mixture of methanol (43.64 parts) and partially hydrogenated soybean oil (100 parts), with sodium methoxide (0.50 parts) as the catalyst, was refluxed for 4 hours. After cooling to room temperature, the product was extracted with water several times to wash out the base catalyst and the glycerol generated during the reaction. The mixture of FAMEs was dried on a rotary evaporator at 80° C. under high vacuum for several hours.

Step 2: Epoxidation of FAMEs from Partially Hydrogenated Soybean Oil

The mixture of FAMEs (100 parts) was epoxidized using 30% hydrogen peroxide (59.9 parts) and acetic acid (10.58 parts), catalyzed by Amberlite-IR-120H (7.15 parts). Toluene (42.88 parts) was added in order to improve the miscibility between the oil and hydrogen peroxide. The epoxidation was carried out at 80° C. for 6 hours. The product was then washed with water till the pH of the aqueous phase was ~7. The mixture of epoxidized FAMEs was then dried on a rotary evaporator at 80° C. under high vacuum (<1 mm Hg) for a few hours. The product had an EOC of 3.93%.

Step 3: Hydrogenation of Epoxidized FAMEs

The mixture of epoxidized FAMEs (100 parts) was dissolved in isopropanol (100 parts) and hydrogenated under 400 psi pressure at 120° C., catalyzed by 20 wt % of Ni catalyst (Ni, 25% blended with saturated fat (PRICAT 9920 from Engelhardt) for 30 hours. The product which was a low melting waxy solid, had a OH# of 128 mg KOH/g and EOC of 0.05%.

Step 4: Polymerization Hydroxylated FAMEs

The polymerization was carried out using the hydroxylated FAMEs (100 parts) and TMP (4.80 parts) at 220° C., catalyzed by Fascat (R)-4350 (0.52 parts). The reaction was carried out at 220° C. for 3 hours without a vacuum, followed by heating at 220° C. under medium vacuum (50-100 mm Hg) for 1 hour. Finally a high vacuum (1-2 mm Hg) was applied for about 1.5 hrs, by which time the pressure inside the system dropped to <1 Torr. The product was a low viscous liquid with a light yellow color.

| OH # (mg KOH/g) | Acid # (mg KOH/g) | Viscosity (Pa·s) | Mw | Mn | Mw/Mn |
|---|---|---|---|---|---|
| 30 | 0.69 | 0.98 | 2233 | 1862 | 1.2 |

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A method of making a polyester polyol from a natural oil-based starting composition, the method comprising the steps of:
   (a) providing a starting composition comprising up to about 95% weight monounsaturated fatty acids/alkyl esters derived from natural oils;
   (b) epoxidizing at least a portion of carbon-carbon double bonds in the starting composition to form an epoxidized fatty acid/alkyl ester composition;
   (c) drying the epoxidized fatty acid/alkyl ester composition to provide a dried epoxidized fatty acid/alkyl ester composition;
   (d) reacting the dried epoxidized fatty acid/alkyl ester composition with an alcohol or hydrogen to ring-open at least a portion of the epoxide groups to form a composition comprising hydroxylated fatty acids/alkyl esters, wherein the hydroxylated fatty acids/alkyl esters comprise a secondary alcohol; and
   (e) reacting the hydroxylated fatty acid/alkyl ester composition with a multifunctional ester-reactive initiator compound according to the formula

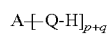

where: A is an organic group; with the proviso that A does not contain an ester of a monofunctional alcohol;
   (p+q) is an integer greater than or equal to 2; and
   -Q-H are independently ester-reactive functional groups, such as alcohols (i.e., -Q- is —O—) and amines (i.e., -Q- is

to form the polyester polyol.

2. A method of making a polyester polyol, the method comprising the steps of:
   (a) providing a starting composition comprising monounsaturated fatty acids/alkyl esters; and polyunsaturated fatty acids/alkyl esters;
   (b) partially hydrogenating the starting composition to convert at least a portion of the polyunsaturated fatty acids/alkyl esters to monounsaturated fatty acids/alkyl esters; wherein after partial hydrogenation the starting composition comprises a hydrogenated composition, wherein the hydrogenated composition comprises up to about 95% weight monounsaturated fatty acids/alkyl esters;
   (c) epoxidizing at least a portion of carbon-carbon double bonds in the hydrogenated composition to form an epoxidized fatty acid/alkyl ester composition;
   (d) drying the epoxidized fatty acid/alkyl ester composition to provide a dried epoxidized fatty acid/alkyl ester composition:
   (e) reacting the dried epoxidized fatty acid/alkyl ester composition with an alcohol or hydrogen to ring-open at least a portion of the epoxide groups to form a composition comprising hydroxylated fatty acids/alkyl esters, wherein the hydroxylated fatty acids/alkyl esters comprise a secondary alcohol; and (f) reacting the hydroxylated fatty acid/alkyl ester composition with a multifunctional ester-reactive initiator compound according to the formula

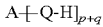

where: A is an organic group; with the proviso that A does not contain an ester of a mono functional alcohol;
(p+q) is an integer greater than or equal to 2; and
-Q-H are independently ester-reactive functional groups, such as alcohols (i.e., -Q- is —O—) and amines (i.e., -Q- is

to form the polyester polyol.

3. A method of making a polyester polyol, the method comprising the steps of:
(a) providing a natural oil;
(b) epoxidizing at least a portion of carbon-carbon double bonds in the natural oil to form an epoxidized natural oil;
(c) drying the epoxidized natural oil to provide a dried epoxidized natural oil;
(d) reacting the dried epoxidized natural oil with an alcohol or hydrogen to ring-open at least a portion of the epoxide groups to form a composition comprising a hydroxylated natural oil, wherein the hydroxylated natural oil comprises a secondary alcohol;
(e) transesterifying or hydrolyzing the hydroxylated natural oil to form a hydroxylated composition comprising:
  (i) up to about 95% weight monohydroxylated fatty acids/alkyl esters; and
  (ii) at least one of: saturated fatty acids/alkyl esters or polyhydroxylated fatty acids/alkyl esters; and
(f) reacting the hydroxylated composition with a multifunctional ester-reactive initiator compound according to the formula

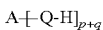

where: A is an organic group; with the proviso that A does not contain an ester of a monofunctional alcohol;
(p+q) is an integer greater than or equal to 2; and
-Q-H are independently ester-reactive functional groups, such as alcohols (i.e., -Q- is —O—) and amines (i.e., -Q- is

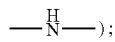

to form the polyester polyol.

4. The method of claim 1, wherein the step of providing a starting composition comprising up to about 95% weight of monounsaturated fatty acids/alkyl esters derived from natural oils comprises:
(a) providing a natural oil; and
(b) hydrolyzing or transesterifying the natural oil to form a starting composition comprising: (i) monounsaturated fatty acids/alkyl esters; and (ii) one or more of: saturated fatty acids/alkyl esters and polyunsaturated fatty acids/alkyl esters.

5. The method of claim 3, wherein the method further includes the step of: partially hydrogenating the natural oil.

6. The method of claim 1, wherein the monounsaturated fatty acid/alkyl ester is C9-C10 monounsaturated.

7. The method of claim 6, wherein the C9-C10 monounsaturated fatty acid/alkyl ester comprises methyl oleate, ethyl oleate, propyl oleate, isopropyl oleate, butyl oleate and isobutyl oleate.

8. The method of claim 1, wherein the monounsaturated fatty acid/alkyl ester is C5-C6 monounsaturated.

9. The method of claim 1, wherein the monounsaturated fatty acid/alkyl ester is C6-C7 monounsaturated.

10. The method of claim 1, wherein the monounsaturated fatty acid/alkyl ester is C11-C12 monounsaturated.

11. The method of claim 1, wherein the monounsaturated fatty acid/alkyl ester is C13-C14 monounsaturated.

12. The method of claim 1, wherein the multifunctional ester-reactive initiator compound is a polyol, a polyamine, or an aminoalcohol.

13. The method of claim 1, wherein the multifunctional ester-reactive initiator is selected from the group consisting of neopentylglycol; 1,2-propylene glycol; 1,3-propane diol, trimethylolpropane, pentaerythritol, sorbitol, sucrose, glycerol, alkanediols, 1,6-hexanediol, 2,5-hexanediol, 1,4-butanediol, 1,4-cyclohexane diol, ethylene glycol, diethylene glycol, triethylene glycol, tetraethylene glycols, polyetheyleneglycols, 9(1)-hydroxymethyloctadecanol, 1,4-bishydroxymethyleyclohexane; Dimerol alcohol, bisphenol A, hydrogenated bisphenol, 1,2,6-hexanetriol, ethanolamine, diethanolamine, triethanolamine, natural oil-based polyols, any of the aforementioned where at least one of the alcohol or amine groups present therein has been reacted with ethylene oxide, propylene oxide, or butylene oxide and mixtures thereof.

14. The method of claim 1, wherein the multifunctional ester-reactive initiator is trimethylolpropane.

15. The method of claim 1, wherein the polyester polyol is a triol.

16. The method of claim 1, wherein the polyester polyol has a number average functionality (Fn) ranging from about 1.5 to about 10.

17. The method of claim 1, wherein the polyester polyol has a number average functionality (Fn) ranging from about 2.5 to about 3.5.

18. The method of claim 1, wherein the polyester polyol has a hydroxyl number that ranges from about 20 to about 500 mg KOH/g.

19. The method of claim 1, wherein the polyester polyol is a triol having a hydroxyl number ranging from about 28 to about 60 mg KOH/gram.

20. The method of claim 1, wherein the polyester polyol has a Mn ranging from about 2000 Da to about 4000 Da.

21. The method of claim 1, wherein the polyester polyol has an iodine value (IV) that is less than about 50.

22. A polyester polyol produced by the method of claim 1.

23. The method of claim 1, wherein the starting composition comprises about 65% weight to about 94% weight monounsaturated fatty acids/alkyl esters.

24. The method of claim 1, wherein the starting composition comprises about 70% weight to about 90% weight monounsaturated fatty acids/alkyl esters.

25. The method of claim 2, wherein after partial hydrogenation the starting composition comprises about 70% weight or greater monounsaturated fatty acids/alkyl esters.

* * * * *